United States Patent
Haran et al.

(10) Patent No.: US 12,022,779 B2
(45) Date of Patent: Jul. 2, 2024

(54) SYSTEM AND METHOD FOR TURNING IRRIGATION PIVOTS INTO A SOCIAL NETWORK OF AUTONOMOUS AI FARMING ROBOTS

(71) Applicant: AUTONOMOUS PIVOT LTD., Tel Aviv-Jaffa (IL)

(72) Inventors: Yossi Haran, Modiin (IL); Yair Sharf, Aloney Aba (IL); Yuval Aviel, Modi'in (IL)

(73) Assignee: AUTONOMOUS PIVOT LTD., Tel Aviv-Jaffa (IL)

( * ) Notice: Subject to any disclaimer, the term of this patent is extended or adjusted under 35 U.S.C. 154(b) by 786 days.

(21) Appl. No.: 17/056,565

(22) PCT Filed: May 21, 2019

(86) PCT No.: PCT/IL2019/050573
§ 371 (c)(1),
(2) Date: Nov. 18, 2020

(87) PCT Pub. No.: WO2019/224817
PCT Pub. Date: Nov. 28, 2019

(65) Prior Publication Data
US 2021/0169023 A1 Jun. 10, 2021

Related U.S. Application Data

(60) Provisional application No. 62/674,043, filed on May 21, 2018.

(51) Int. Cl.
*A01G 25/16* (2006.01)
*A01G 25/09* (2006.01)
(Continued)

(52) U.S. Cl.
CPC ........... *A01G 25/16* (2013.01); *A01G 25/092* (2013.01); *B05B 12/12* (2013.01); *G01N 33/246* (2013.01);
(Continued)

(58) Field of Classification Search
CPC ...... A01G 25/16; A01G 25/092; B05B 12/12; G01N 33/246; G01S 13/865; G01S 13/867; G01S 13/885
See application file for complete search history.

(56) References Cited

U.S. PATENT DOCUMENTS 4,662,563 A 5/1987 Wolfe
5,088,561 A * 2/1992 Jurgena ................ A01B 69/004
180/401
(Continued)

FOREIGN PATENT DOCUMENTS

AU 6225586 A 3/1987
CN 101393456 A 3/2009
(Continued)

OTHER PUBLICATIONS

State Intellectual Property Office of P. R. China, Notification of First Office Action for Chinese Application No. 201980045749.9, dated Jan. 24, 2022, 22pp.
(Continued)

*Primary Examiner* — Peter M Bythrow
*Assistant Examiner* — Nazra Nur Waheed
(74) *Attorney, Agent, or Firm* — The Roy Gross Law Firm, LLC; Roy Gross

(57) ABSTRACT

A method of automatically managing a center pivot irrigation machine comprising steps of: (a) providing at least one center pivot irrigation machine and positioning said center pivot irrigation machine such that said center pivot irrigation machine is movable within an irrigated plot around a center
(Continued)

thereof; (b) providing a ground penetration radar; (c) mounting said ground penetration radar on said center pivot irrigation machine; (d) moving said center pivot irrigation machine about said center of said irrigated plot; (e) scanning said irrigated by said ground penetration radar at frequencies ranging between 200-1200 MHz; (f) calculating a distribution of soil moisture over a depth from a soil surface; and (g) creating an irrigation plan according to said distribution.

4 Claims, 22 Drawing Sheets

(51) Int. Cl.
*B05B 12/12* (2006.01)
*G01N 33/24* (2006.01)
*G01S 13/86* (2006.01)
*G01S 13/88* (2006.01)

(52) U.S. Cl.
CPC .......... *G01S 13/865* (2013.01); *G01S 13/867* (2013.01); *G01S 13/885* (2013.01)

(56) References Cited

U.S. PATENT DOCUMENTS

| | | |
|---|---|---|
| 8,849,523 B1 | 9/2014 | Chan et al. |
| 9,733,355 B2 | 8/2017 | Chan et al. |
| 10,073,074 B1 | 9/2018 | Kumar et al. |
| 2002/0196177 A1 | 12/2002 | Johansson et al. |
| 2004/0201385 A1 | 10/2004 | Drnevich et al. |
| 2014/0365084 A1 | 12/2014 | Chan et al. |
| 2016/0088807 A1 | 3/2016 | Bermudez Rodriguez et al. |
| 2017/0038749 A1 | 2/2017 | Mewes et al. |
| 2017/0235471 A1 | 8/2017 | Schøler et al. |
| 2017/0251589 A1 | 9/2017 | Tippery et al. |
| 2017/0374323 A1* | 12/2017 | Gornik ................ A01B 79/005 |
| 2018/0325012 A1* | 11/2018 | Ferrari ................ A01B 69/008 |
| 2018/0348714 A1 | 12/2018 | Larue |
| 2019/0124859 A1 | 5/2019 | Larue |

FOREIGN PATENT DOCUMENTS

| | | |
|---|---|---|
| CN | 102388791 A | 3/2012 |
| CN | 104777286 A | 7/2015 |
| CN | 104885884 A | 9/2015 |
| CN | 104938131 A | 9/2015 |
| CN | 107121444 A | 9/2017 |
| CN | 109496797 A | 3/2019 |
| CN | 112384062 A | 2/2021 |
| DE | 102011056754 A1 | 6/2013 |

OTHER PUBLICATIONS

Adeyemi, Olutobi, et al. Advanced monitoring and management systems for improving sustainability in precision irrigation. Sustainability, 2017, 9.3: 353. Adeyemi at el. Feb. 28, 2017 (Feb. 28, 2017).
PCT Search Report for International Application No. PCT/IL2019/050573 dated Sep. 16, 2019, 5 pp.
PCT Written Opinion for International Application No. PCT/IL2019/050573 dated Sep. 16, 2019, 6 pp.
PCT Preliminary Report on Patentability for International Application No. PCT/IL2019/050573 dated Nov. 24, 2020, 7 pp.
United States Patent and Trademark Office Action for U.S. Appl. No. 17/859,590, dated Sep. 1, 2023, 28pp.
Chinese Office Action received for Chinese Patent Application No. 202210641103.0, dated Aug. 8, 2023, 11pp.
Adeyemi, O.; Grove, I.; Peets, S.; Norton, T. (2017). Advanced Monitoring and Management Systems for Improving Sustainability in Precision Irrigation. Sustainability 2017, 9, 353. https://doi.org/10.3390/su9030353.

* cited by examiner

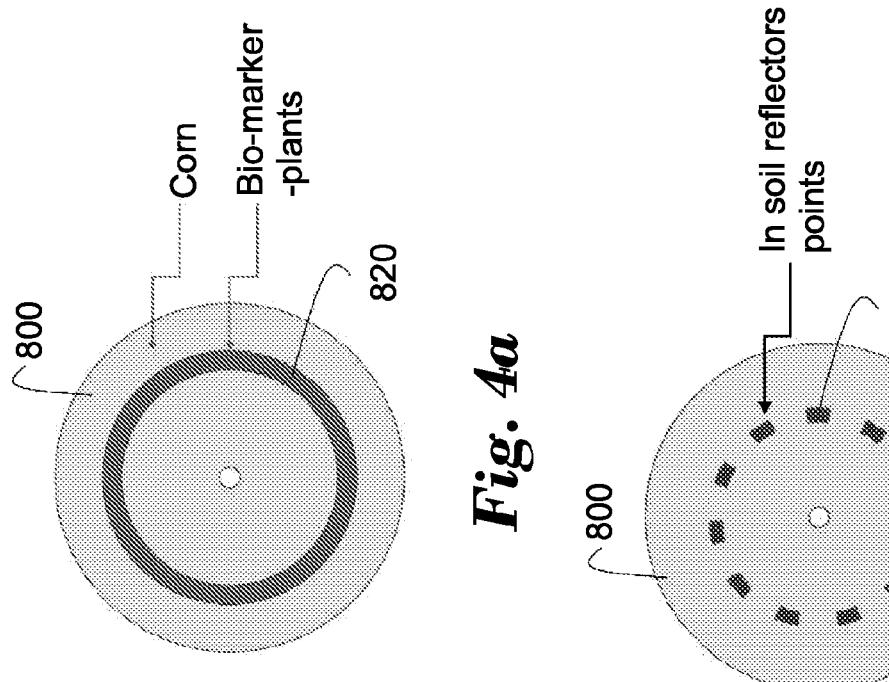
*Fig. 4a*
*Fig. 4b*
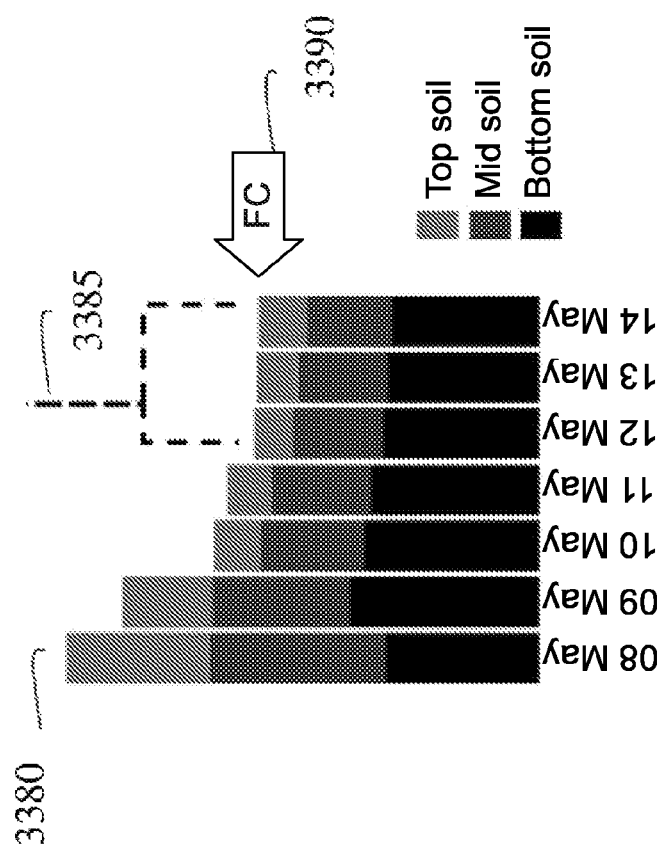
*Fig. 3c*

SYSTEM AND METHOD FOR TURNING IRRIGATION PIVOTS INTO A SOCIAL NETWORK OF AUTONOMOUS AI FARMING ROBOTS

CROSS REFERENCE TO RELATED APPLICATIONS

This application is a National Phase of PCT Patent Application No. PCT/IL2019/050573 having International filing date of May 21, 2019, entitled "SYSTEM AND METHOD FOR TURNING STANDARD IRRIGATION PIVOTS INTO A SOCIAL NETWORK OF AUTONOMOUS AI FARMING ROBOTS", which claims the benefit of priority of U.S. Provisional Application No. 62/674,043, filed on May 21, 2018. The contents of the above applications are all incorporated by reference as if fully set forth herein in their entirety.

FIELD OF THE INVENTION

The present invention relates to irrigation devices and, more particularly, to automated irrigating and fertilizing system configured for sensing and analyzing climatic parameters and establishing a schedule of irrigation and fertilization.

BACKGROUND OF THE INVENTION

Center pivot irrigation is a form of overhead sprinkler irrigation consisting of several segments of pipe with sprinklers positioned along their length, joined together and supported by trusses, and mounted on wheeled towers. The machine moves in a circular pattern and is fed with water from the pivot point at the center of the circle. The outside set of wheels sets the master pace for the rotation.

Smart irrigation fertilization systems tailor watering/fertilization schedules and run automatically to meet specific plant needs. This approach significantly improves outdoor efficiency of water and fertilizers use.

At different stages of growth, plants consume different amounts of water and fertilizers. In addition, the specific amounts to be provided to the plants depend on real climatic conditions (temperature, relative humidity and wind speed). Hence, there is a long-felt and unmet need for development of a method of automatically managing a plurality of center pivot irrigation machines such the amounts of water and fertilizers are applied to the cultivated plants according to specific climatic conditions sensed in real time.

SUMMARY OF THE INVENTION

It is hence one object of the invention to disclose a method of automatically managing a center pivot irrigation machine. The aforesaid method comprises steps of: (a) providing at least one center pivot irrigation machine and positioning said center pivot irrigation machine such that said center pivot irrigation machine is movable within an irrigated plot around a center thereof; (b) providing a proximity soil sensor such as a ground penetration radar; (c) mounting said proximity soil sensor on said center pivot irrigation machine; (d) moving said center pivot irrigation machine about said center of said irrigated plot; (e) scanning said irrigated by said ground penetration radar at frequencies ranging between 20-2000 MHz and 20-1000 kHz; (f) calculating a distribution of soil moisture over a depth from a soil surface; and (g) creating an irrigation plan according to said distribution.

A further object of the invention is to provide the method comprising steps of scanning a no-object area and subtracting obtained no-object data from data corresponding to irrigated area.

A further object of the invention is to provide the method comprising a step of short, open load calibration.

A further object of the invention is to provide the step of subtracting obtained no-object data from data corresponding to irrigated area comprising converting both scans into the time domain signals.

A further object of the invention is to provide the step of calculating a distribution of soil moisture over a depth from a soil surface comprising cross-correlating a subtraction result with the ideal time domain transmitted signal in order to locate the most prominent reflection.

A further object of the invention is to provide the method comprising a step of applying bandpass filters to a time window surrounding a most prominent reflection in order to calculate a response in at least two frequency bands corresponding to at least two penetration depths.

A further object of the invention is to provide the method comprising a step of capturing an optical image of at least a part of said irrigated plot and recognizing a position of a field of view of said ground penetration radar.

A further object of the invention is to provide the method comprising steps of collecting soil properties data and monitoring said properties and reporting results to a user.

A further object of the invention is to provide the method comprising steps of collecting soil properties data and monitoring said properties and reporting results to a user.

A further object of the invention is to provide the method comprising a step of positioning said proximity soil sensor in at least one of horizontal and vertical directions by at least one of horizontal and vertical arms configured for holding said proximal ground sensor.

A further object of the invention is to provide the method comprising a step of placing at least one RF reflecting member within said soil at a predetermined depth from a soil surface.

A further object of the invention is to provide the method comprising a step of scanning and calculating crop dryness by means of a sensor selected from the group consisting of a wide beam ground penetration radar, a narrow beam ground penetration radar, an optical camera and any combination thereof.

A further object of the invention is to provide the method comprising a step of planting at least one biomarker plant configured for signaling in response to a predetermined event and monitoring said at least one biomarker plant.

A further object of the invention is to provide the method comprising a step of scanning and analyzing soil variability within the field by acquiring actual drying curves and field capacity (FC) by staying static at one location for a predetermined time period.

A further object of the invention is to provide the step of scanning and analyzing soil variability further comprises a dry run scanning FCs in a plurality of locations.

A further object of the invention is to provide a center pivot irrigation machine comprising: a proximity soil sensor configured for obtaining volumetric water content data pertaining to croplands treated by said plurality of center irrigation machines configured for obtaining volumetric water content data pertaining to croplands treated by said plurality of center irrigation machines. The aforesaid center pivot irrigation machines is configured for (a) moving said center pivot irrigation machine about said center of said irrigated plot; (b) scanning said irrigated plot by said proximity soil sensor at (c) calculating a distribution of soil moisture over a depth from a soil surface; and (d) creating an irrigation plan according to said distribution.

A further object of the invention is to a provide method of precise calculating field capacity and salinity; said method comprising: (a) Obtaining data of electromagnetic scanning of a soil; (b) Calculating a soil type and bulk density value; (c) Calculating volumetric water content; (d) Comparing an obtained value of said volumetric water content with compared with threshold; (e) Periodically carrying out a reciprocative scan in locations corresponding to said value of volumetric water content being greater than threshold T; (f) collecting volumetric water content data in said locations with volumetric water content>T; (g) plotting a drying curve for a time period ranging between 3 and 4 days; (h) updating said soil type and bulk density value; (i) calculating field capacity and salinity values.

A further object of the invention is to provide the step of carrying out a reciprocative scan recurring in 2-hour time period.

A further object of the invention is to provide the method comprising a step of evaluating a crop moisture value by subtracting values of said soil water content measured directly from values of said soil water content measured through crop plants.

A further object of the invention is to provide the method comprising a step of measuring a crop moisture value in a GPR beam oriented in parallel to the ground.

A further object of the invention is to provide a method of measuring soil content data, said method being adapted for implementation in a field environment comprising a plurality of plants arranged in a plantation pattern comprising a plurality of row-like elements, wherein said plurality of row-like elements being spaced apart from one another by at least a predetermined distance, whereby for each of which row-like elements at least one adjacent unplanted space is defined; said method comprising the steps of: (a) obtaining a first measurement dataset using a first data sensing device configured for obtaining a first type of measurement dataset comprised in a first field-of-view (FOV), wherein said first data sensing device being accommodated by a first support member in a position at a first height relative to a ground level of said field environment, said first height being determined based on a first threshold; (b) determining, based on data analysis of the first measurement dataset: (i) a location of at least a first row-like element of the plurality of row-like elements; and, (ii) a location of a first adjacent unplanted space corresponding to said first row-like element; and, (c) obtaining a second measurement dataset using a second data sensing device configured for obtaining a second type of measurement dataset comprised in a second FOV, said second data sensing device being accommodated by a second support member in a position at a second height relative to the ground level, said second height being determined based on a second threshold; wherein said obtaining the second measurement dataset is performed while said second data sensing device being spatially translated along a trajectory longitudinally traversing said first adjacent unplanted space, which spatial translation being effected responsive to a control command outputted based on the location of the first adjacent unplanted space determined.

A further object of the invention is to provide the plantation pattern selected from the group consisting of: a linear pattern, wherein said plurality of row-like elements are shaped in a form of straight lines parallel to one another; and, a circular-like pattern, wherein said plurality of row-like elements are shaped in a form of concentric circles of successively increasing radii.

A further object of the invention is to provide the said first and second data sensing devices selected from the group consisting of: a Ground-Penetrating Radar (GPR) antenna; a Micropower Impulse Radar (MIR) antenna; a Light Direction And Ranging (LIDAR) sensor; and any combination thereof.

A further object of the invention is to provide the field environment further comprising a center pivot irrigation system deployed therein, wherein said first support member being comprised in a pivot arm of said center pivot irrigation system.

A further object of the invention is to provide the field environment further comprising a center pivot irrigation system deployed therein, wherein said second support member comprises an articulated arm extending from a pivot arm of said center pivot irrigation system.

A further object of the invention is to provide the first FOV being obtained by means of directing said first data sensing device at an angle towards a ground level of said field environment relative to a perpendicular from a position thereof to the ground level, which angle being selected from a range between about 45 degrees and about 75 degrees.

A further object of the invention is to provide the second FOV being obtained by means of directing said second data sensing device at an angle towards a ground level of said field environment relative to a perpendicular from a position thereof to the ground level, which angle being selected from a range between about 0 degrees and about 20 degrees.

A further object of the invention is to provide the first threshold defined as a function of a maximal height of the plurality of plants, and wherein said second threshold is defined as a function of at least one of: a minimum height of a canopy of the plurality of plants; and, a range of one or more water sprinklers deployed in said field environment.

A further object of the invention is to provide the method comprising determining a structure of said plantation pattern, wherein responsive to a determination that said plantation pattern is linear, performing the further steps of: (a) obtaining a first sine wave pattern associated with the first measurement dataset; (b) obtaining a second sine wave pattern associated with the second measurement dataset; (c) determining, based on the first sine wave pattern, a temporary frequency corresponding to a temporary angle between one or more row-like elements of the plurality of row-like elements and said first support member accommodating said first sensing device; and, (d) isolating within the second measurement dataset, based on the temporary frequency determined and the second sine wave pattern, one or more measurements exhibiting a frequency matching to the temporary frequency, to obtain therefrom minima values representative of measured soil content data.

A further object of the invention is to provide a system useful for measuring soil content data, said system being adapted for deployment in a field environment comprising a plurality of plants arranged in a plantation pattern comprising a plurality of row-like elements, wherein said plurality of row-like elements being spaced apart from one another by at least a predetermined distance, whereby for each of which row-like elements at least one adjacent unplanted space is defined; said system comprising: (a) a first data sensing device configured for obtaining a first type of measurement dataset comprised in a first field-of-view (FOV); (b) a second data sensing device configured for obtaining a second type of measurement dataset comprised in a second FOV; (c) a first support member configured for accommodating said first data sensing device in a position at a first height relative to a ground level of said field environment, said first height being determined based on a first threshold; (d) a second support member configured for accommodating said second data sensing device in a position at a second height relative to the ground level, said second height being determined based on a second threshold; (e) at least one spatial translation mechanism configured for spatially translating said first and second support members in response to control commands, thereby effecting spatial translation of said first and second data sensing devices; (f) an analyzing unit configured for determining, based on data analysis of a first measurement dataset obtained by said first data sensing device: (i) a location of at least a first row-like element of the plurality of row-like elements; and, (ii) a location of a first adjacent unplanted space corresponding to said first row-like element; (g) a control unit configured for outputting, based on the location of the first adjacent unplanted space determined by said analyzing unit, a control command to said spatial translation mechanism in order to spatially translate said second data sensing device along a trajectory longitudinally traversing said first adjacent unplanted space; and, (h) a data collection unit configured for collecting a second measurement dataset obtained by said second data sensing device while traversing said trajectory.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which

FIG. 3c is a graph of a 7 days graph demonstrating a per day (3380) soil water content as measured by the GPR;

FIG. 4a schematically illustrates reference areas for planting crop usable as Bio markers;

FIG. 4b schematically illustrates reflection members inserted into specific depth in the soil;

DETAILED DESCRIPTION OF THE INVENTION

The following description is provided, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a method of automatically managing a plurality of center pivot irrigation machines and a system for doing the same.

Figure 1A:
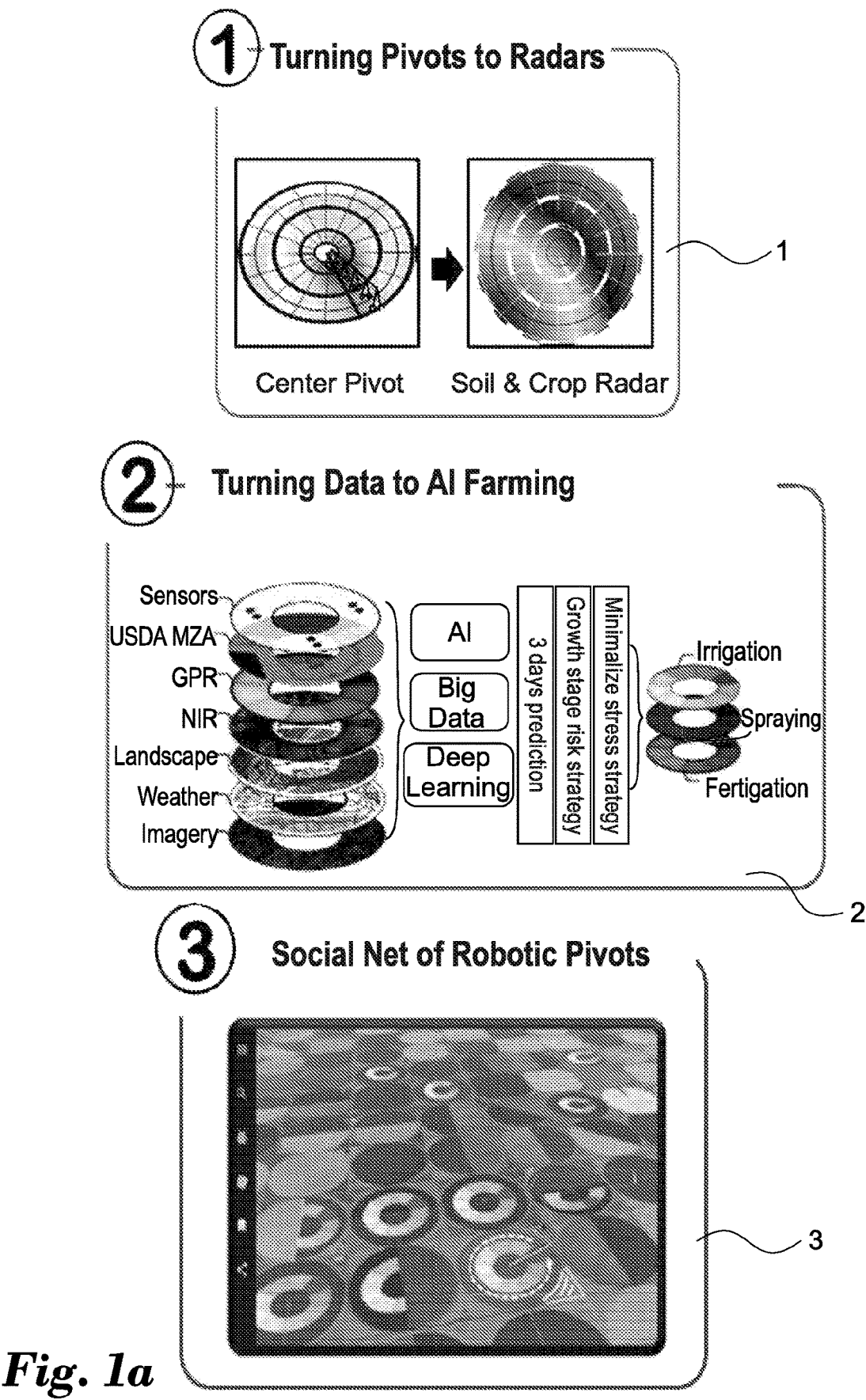
FIG. 1a is a is a conceptual illustration of turning center-pivot irrigation systems into a social network of autonomous ai farming robots in 3 steps.

Reference is now made to FIG. 1a presenting a conceptual illustration of turning center-pivot irrigation systems into a social network of autonomous AI farming robots comprising main three steps of turning center pivot machines into radars (step 1), turning soil and crop data to artificial intellect farming (step 2) and organizing the radars into a social net.

Figure 1B:
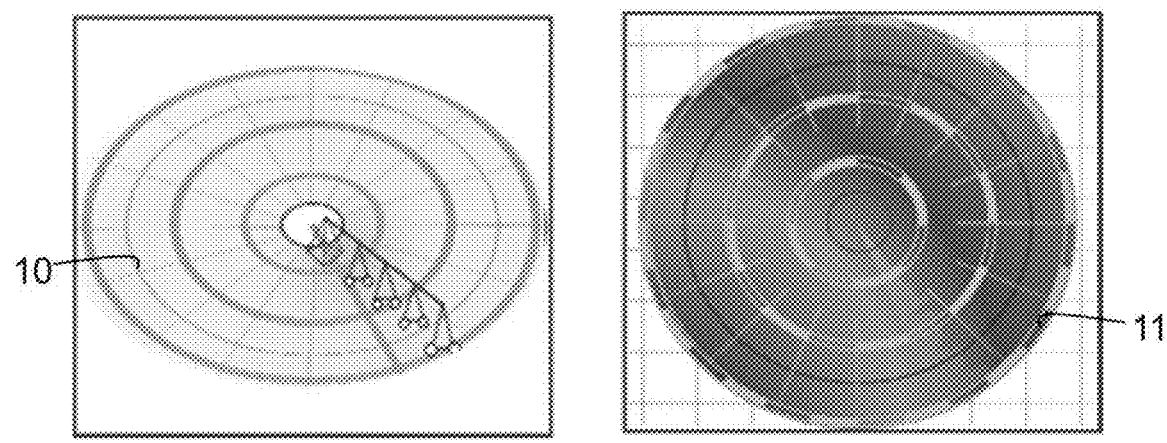
FIG. 1b is a conceptual illustration of turning a standard center-pivot irrigation system into an On-Site Radar with continuous near surface remote sensing of Soil & Crop.

Reference is now made to FIG. 1b illustrating center pivot irrigation machine 10 on irrigated radar's plot 11.

Figure 1C:
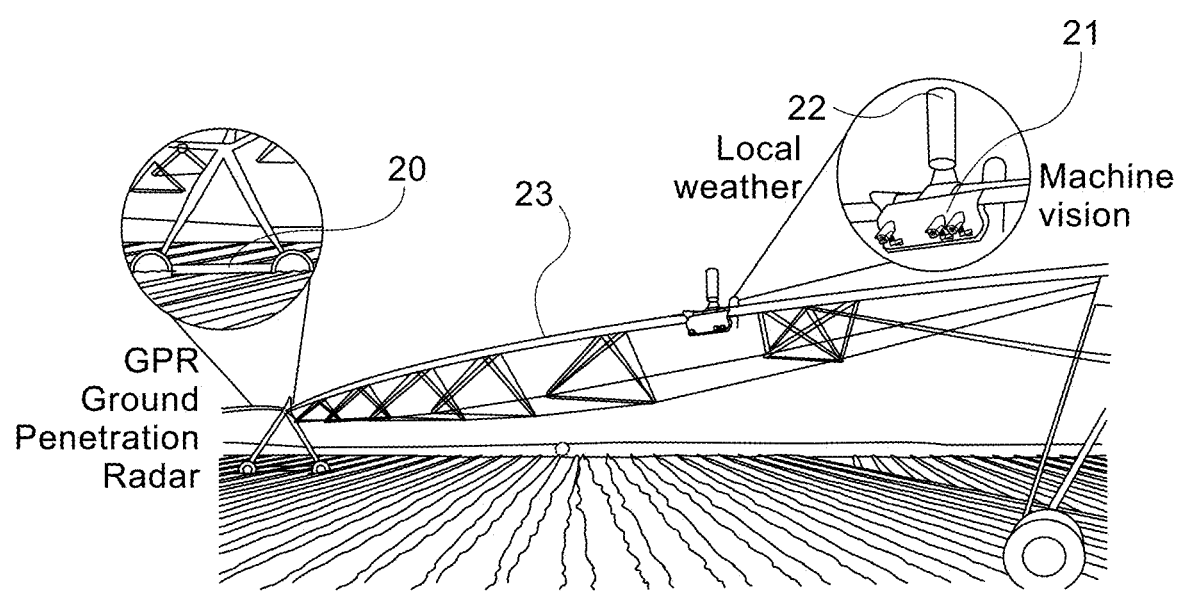
FIG. 1c is a general view of a near surface remote sensors such as ground penetration radar, machine vison and weather sensors mounted on a center pivot irrigation machine.

Reference is now made to FIG. 1c presenting a detailed schematic diagram of center pivot irrigation machine 23 provided with weather sensor 22, machine vision sensor (camera) 21 and ground penetration radar 20.

Figure 1D:
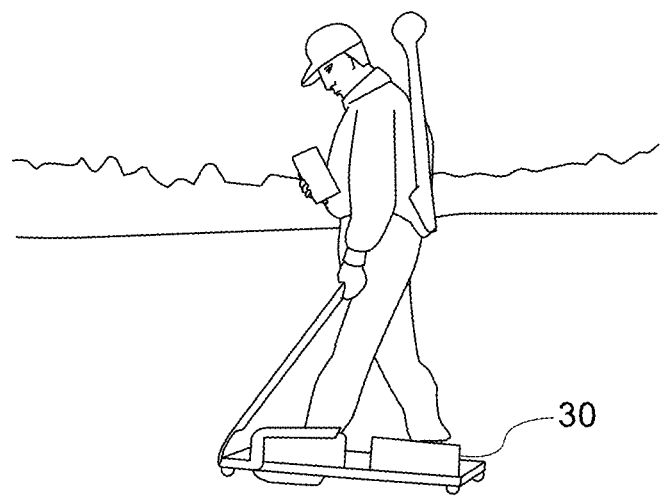
FIG. 1d is a general view of a portable EM scanning device known in the art
Figure 1E:
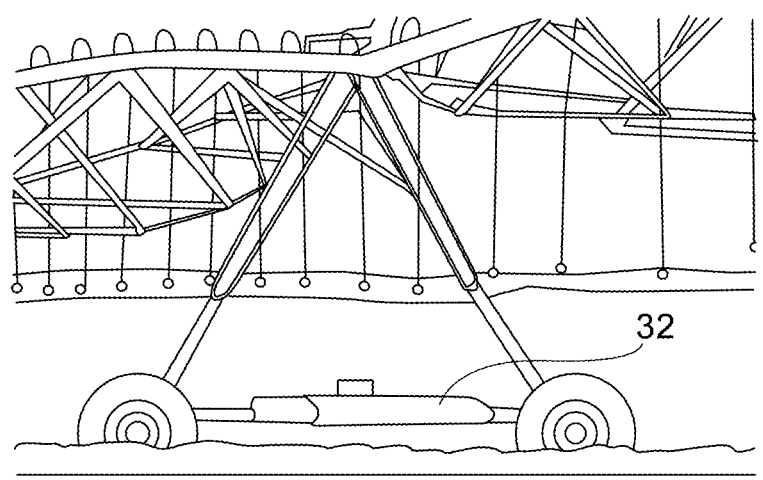
FIG. 1e is a general view of a pivoted EM scanning device.

In FIG. 1d, a general view of portable EM scanning device 30 known in the art is shown while FIG. 1e illustrates a pivoted EM scanning device of the present invention.

Figure 1F:
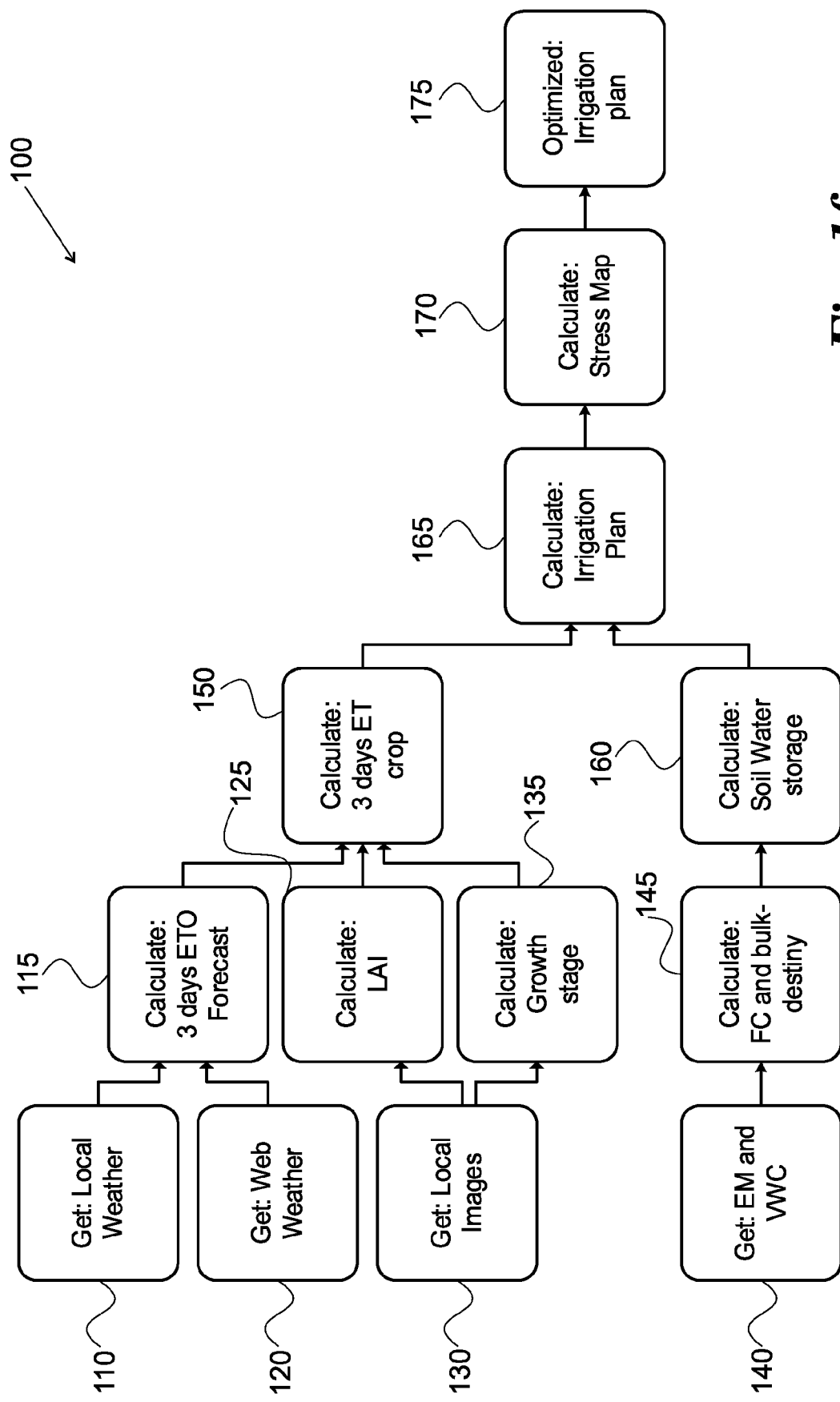
FIG. 1f is a flowchart of a method of establishing an irrigation plan.

Reference is now made to FIG. 1f, showing a flowchart of a method 100 of establishing an irrigation plan which is obtained on the basis of an evapotranspiration forecast, a leave area index, a growth stage and a field capacity and bulk density.

Specifically:

1. Meteorological channel: a local weather details (temperature, relative humidity and wind speed) is obtained at step 110. In parallel, a Web-based weather forecast is provided (step 120). In correlation between the local weather details and Web-based weather forecast, a 3-day evapotranspiration forecast is calculated.

2. Optical channel: local images pertaining to croplands treated by a plurality of center irrigation machines are captured at step 130. The captured images are processed such that a leave area index is calculated (step 125) and a growth stage is determined (step 135). In correlation between 3-day evapotranspiration forecast obtained in the meteorological channel and leave area index/growth stage from the optical channel, a 3-day evapotranspiration forecast updated in view of a real growth stage of a plant within the specific cropland (step 150).

3. Electromagnetic channel: the croplands are scanned by a ground penetration radar at step 140. As a result, volumetric water content is obtained. On the basis of the volumetric water content, values of field capacity and soil bulk density are calculated (step 145). In addition, a value of soil water storage is calculated (step 160).

The previously obtained 3-day evapotranspiration forecast updated in view of a real growth stage and soil water storage constitutes input data for establishing an irrigation plan (step 165). In addition, a stress map integrating all negative factors affecting the cultivated plant is obtained at step 170. An irrigation plan optimized in view of the obtained stress map is established at step 175.

Figure 2A:
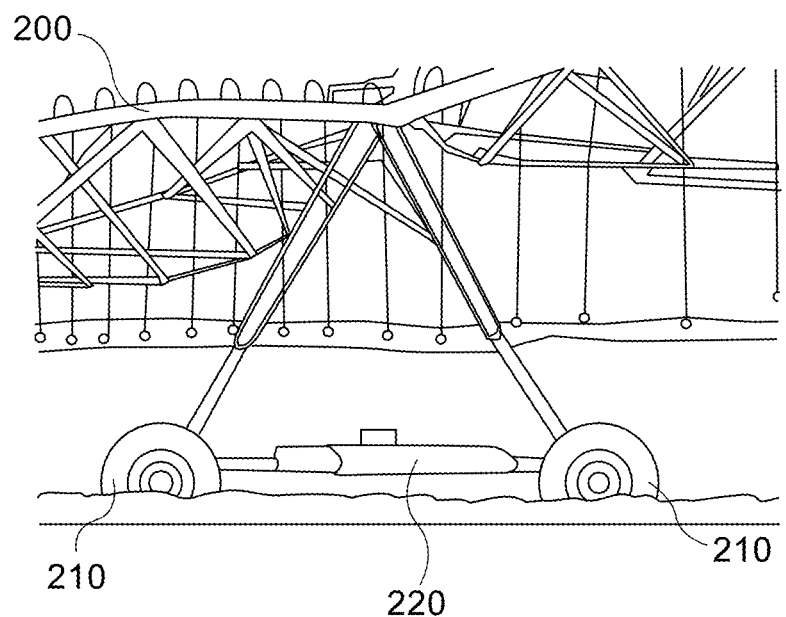
FIG. 2a is a general view of a ground penetration radar mounted on a center pivot irrigation machine.

Reference is now made to FIG. 2a presenting a general view of a ground penetration radar mounted on a center pivot irrigation machine. As known in the art, center pivot irrigation machine 200 moves around a pivot point (not shown). Ground penetration radar 220 is mounted between wheels 210 such that the ground is scanned within a rut (not shown) made by wheels 210. The rut is free of the cultivated plants. Thus, the obtained ground scan data are not distorted by the plants cultivated on the specific cropland.

Figure 2B:
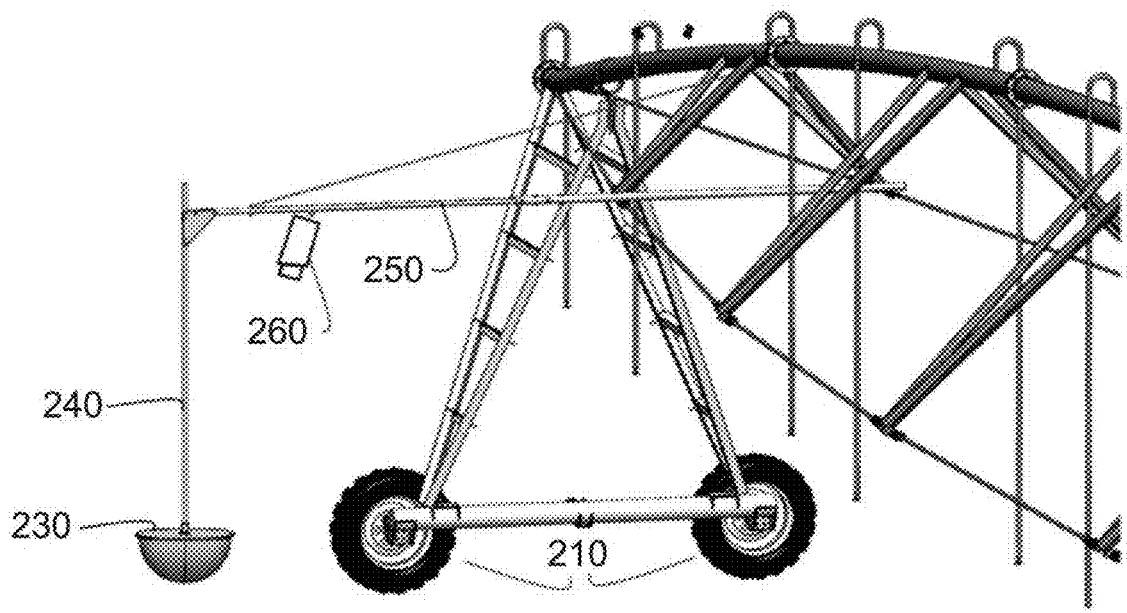
FIG. 2b is a general view of a directional ground penetration radar mounted on a center pivot irrigation machine.

Reference is now made to FIG. 2b is a general view of a directional ground penetration radar mounted on a center pivot irrigation machine 210 pivotally movable on wheels 230. Numeral 240 refers to a directional multi-band GPR. A position of GPR 240 is adjustable in a vertical direction by vertical arm 250 configured for varying a height of GPR 240 over the ground; and a horizontal direction by horizontal arm 250 configured for varying a measuring distance before the sprinklers. Camera 260 is configured for real time visual control of GPR position relative to crop plants.

GPR 230 comprises (a) an antenna (not shown) configured for radiating and receiving radiation of the desired wave length (in this case 20-2000 MHz and 20-1000 kHz), (b) a transmitting/receiving device configured for transmitting electrical signals of the desired wavelength and receiving a response from the ground, and (c) a computing device to manage transmit/receive and store measured data. Operation of the GPR may be done in the following sequence:

SOL (short, open load) instrument calibration,
a full frequency span scan with no objects in the field of view of the GPR in order to obtain a system noise level, and
a full frequency span scan of the desired object.

According to one embodiment of the present invention, data processing of measured GPR data is performed by the following way:
converting both scans into the time domain signals,
subtracting the no object scan data from object scan data to eliminate any system noise,
cross-correlating the result with the ideal time domain transmitted signal in order to locate the most prominent reflection.
applying bandpass filters to a time window surrounding the most prominent reflection in order to calculate a response in different frequency bands.

The response of the different frequency bands is then used to determine soil water content profile.

According to one embodiment of the present invention, the center pivot irrigation machine is equipped with GPR capable to emit at least one narrow beam and one wide beam. The computing device is configured for acquiring soil water content through tall crop based on the different in signals received when using the narrow beam and when using the wide beam.

Figure 14A:
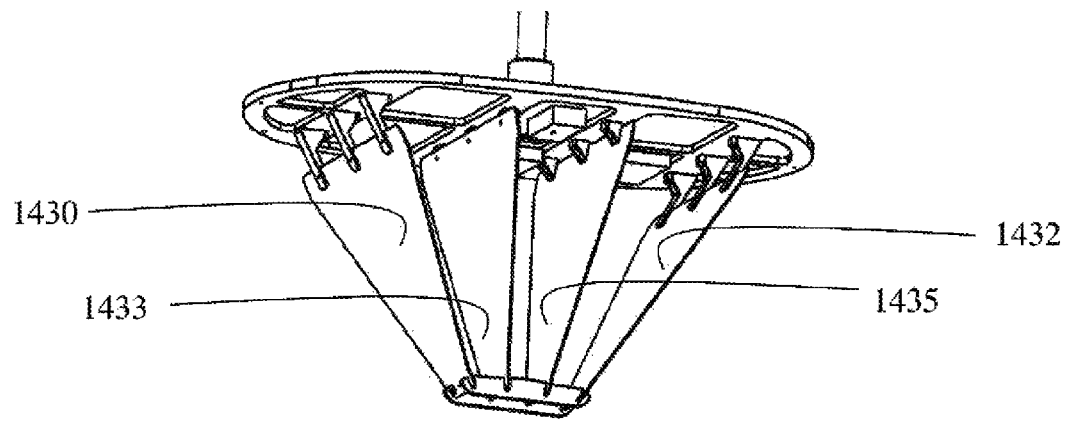
FIG. 14a illustrates an antenna configured for emitting narrow and wide beams.

Controlling the beam width can be done by contacting and disconnecting antenna components within the multi-bend antenna array (for example an array of 4 component 1430+1432+1433+1435 in FIG. 14a emits a narrow bean while 2 components 1433+1435 of FIG. 14a emits wide beam).

Pivot equipped with GPR and Camera (260) will enable analyzing methods for acquiring the soil water content through a tall crop based on image processing for classifying the segments scanned by the GPR Installing the GPR on adjustable vertical arm (240) for determining the above ground height, and: adjustable horizontal arm for determining the measuring distance before the sprinklers; (250), enable the acquiring the soil water content while irrigating.

Pivot equipped with GPR and dry-run scanning methods:
For acquiring the soil water content
For acquiring actual drying curves per segment
For acquiring actual FC per segment
For acquiring actual drying curves and/or FC and water content by staying static at one location for a required time period Pivot equipped with GPR for scanning and analyzing crop dryness utilizing the wide/narrow beam methods and or the GPR and camera methods describe previously as a method for measuring the soil water content through tall crop can also be used as a tool for evaluating crop dryness or crop level of moisture simply by subtracting the values of soil water content from values the received when measuring through the crop.

Figure 3A:
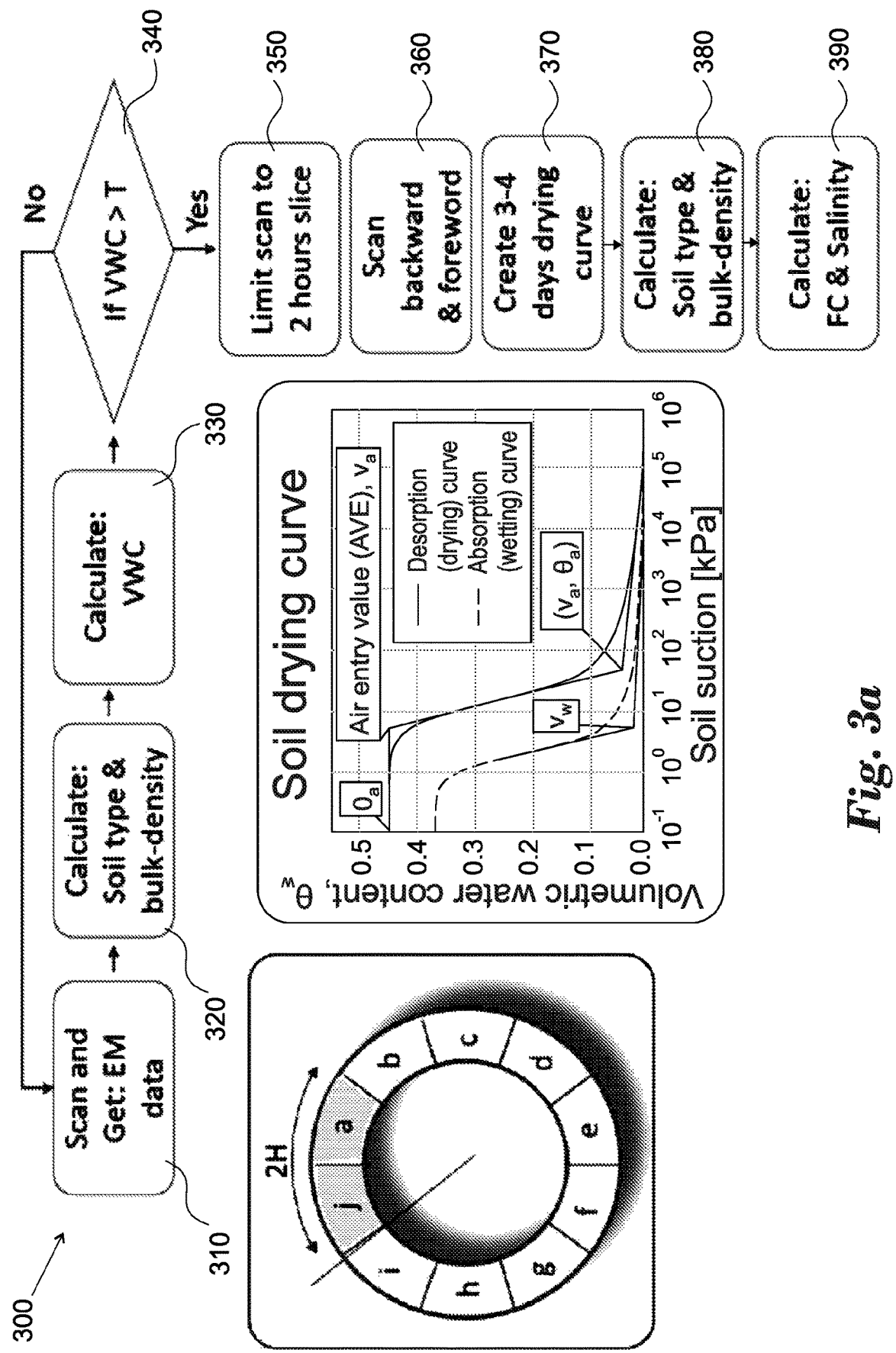
FIG. 3a is a flowchart of a real time method for calculating soil properties.

Reference is now made to FIG. 3a showing a flowchart of method 300 of precise calculation of field capacity and salinity. Data obtained by means of electromagnetic scanning (step 310) are used for calculation of soil type and bulk density (step 320) and then volumetric water content is calculated (step 330). At step 340, the obtained value of volumetric water content is compared with threshold T (step 340). If the value of volumetric water content is greater than threshold T, a more detailed scan is carried out. Specifically, the scan is limited to a 2 hour slice (step 350). The locations characterized by volumetric water content>T are reciprocatively scanned at step 360. On the basis of obtained data of detailed scan, a 34-day drying curve is plotted (step 370). Then, the updated soil type and value of bulk density are calculated (step 380). Finally, field capacity and salinity are obtained (step 390).

Figure 3B:
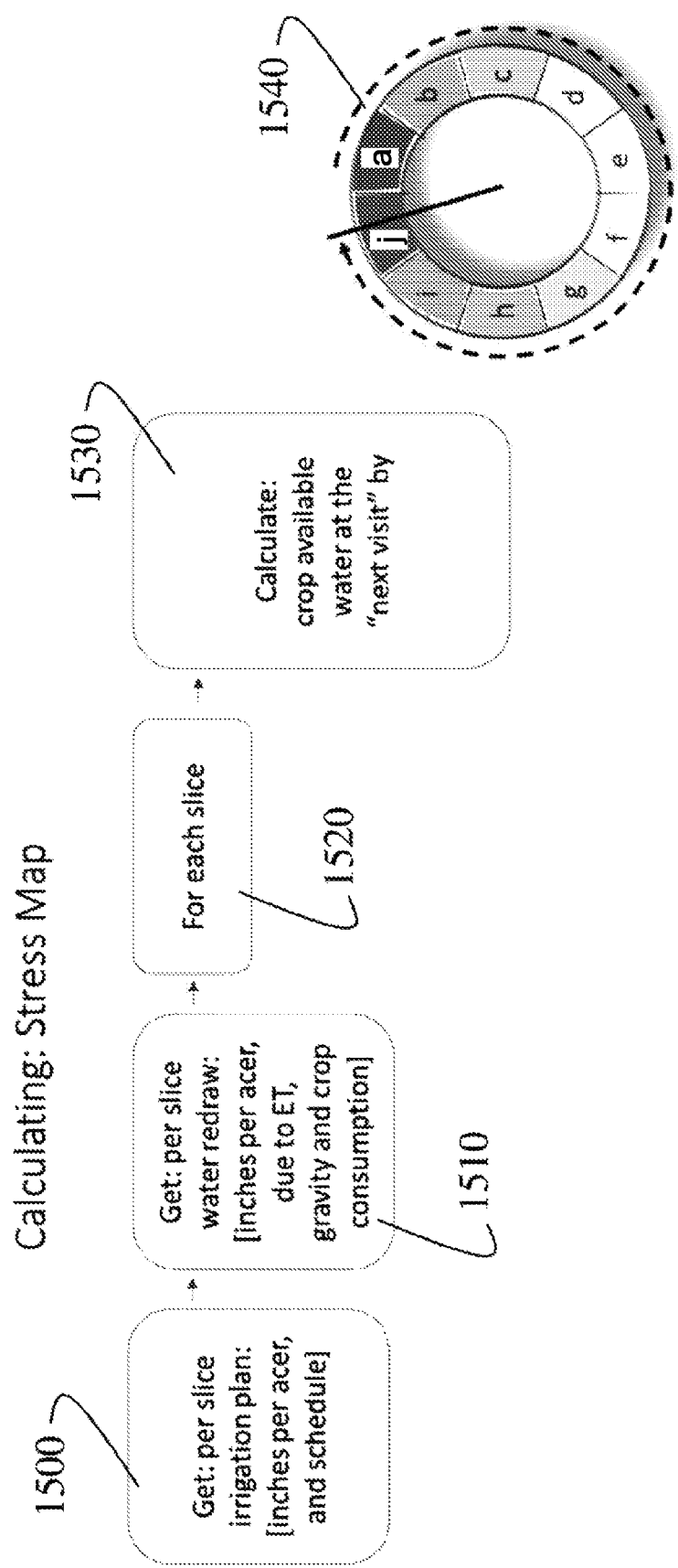
FIG. 3b is a flowchart for calculating estimated water stress.

Reference is now made to FIG. 3b is a flowchart for calculating an estimated water stress to be developed between 2 visits of the pivot in a specific slice. At step 1500, getting a per-slice irrigation plan is performed. After that, getting a per-slice water redraw (step 1510) is carried out. At step 1530, crop available water at "next visit" within each slice is calculated. The calculated crop available water data are displayed at step 1540.

Reference is now made to FIG. 3c is a 7 days graph demonstrating a per day (3380) soil water content as measured by the GPR. A pivot equipped with GPR for scanning and analyzing soil variability within the field by acquiring actual drying curves and field capacity (FC) by staying static at one location for a required time period (the GPR is acting as static soil sensor). The described method takes advantage at off-season time, before emerging, at early growth stage and stand-by for rain event that bring the field above field capacity than wait until the values of soil water content are statics (typically 3 days depend on soil type) (3385) the value at this static condition consider FC (3390) and then dry run the pivot for scanning the values of FCs in different location in the field it is expected to receive similar values if the soil is homogeneous and variable values if the soil is not homogeneous.

Figure 14B:
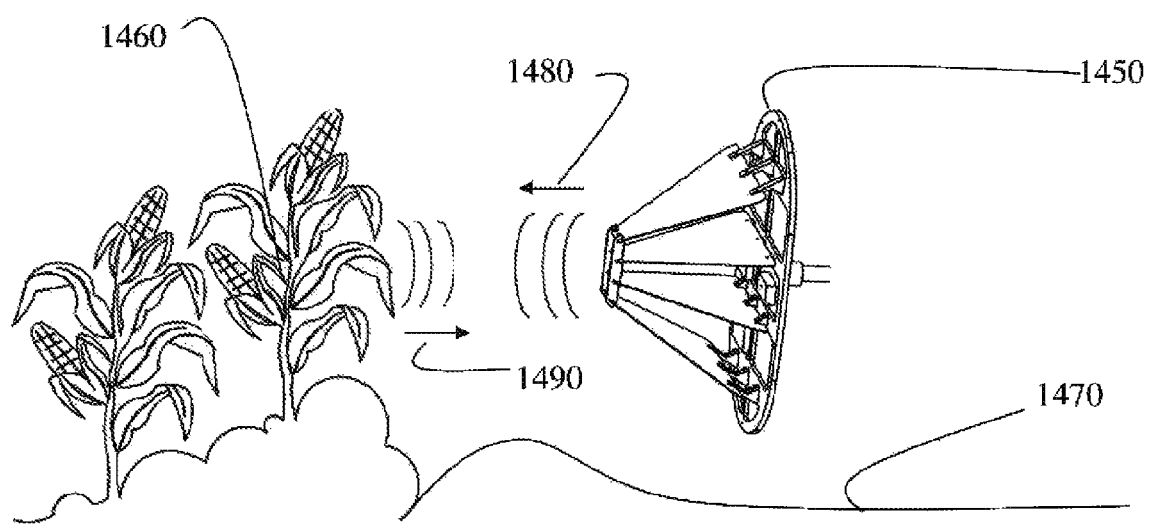
FIG. 14b is a schematic diagram illustrating a GPR beam oriented in parallel to the ground.

According to one embodiment of the present invention, moisture value of crop plants 1460 is measured in GPR beam 1480 created by antenna 1450 oriented in parallel to the ground (see FIG. 14b).

Reference is now made to FIG. 4a schematically illustrate reference areas for determining a planting crop to be use as Bio markers FIG. 4a shows circular cropland 800 typical for canter pivot irrigation systems of corn including a concentrically arranged ring formed by biomarker plants 820 having more sensitive faster respond to specifics stress conditions with known spectral characteristics. The biomarker plants can be used as reference objects for early alert of strass long before it starts showing on the commercial crop.

Reference is now made to FIG. 4b schematically illustrate of reflection surface members 840 inserted into specific subsurface depth in the soil. As reference areas for reflectors can be used as reference objects for GPR calibration.

Figure 5:
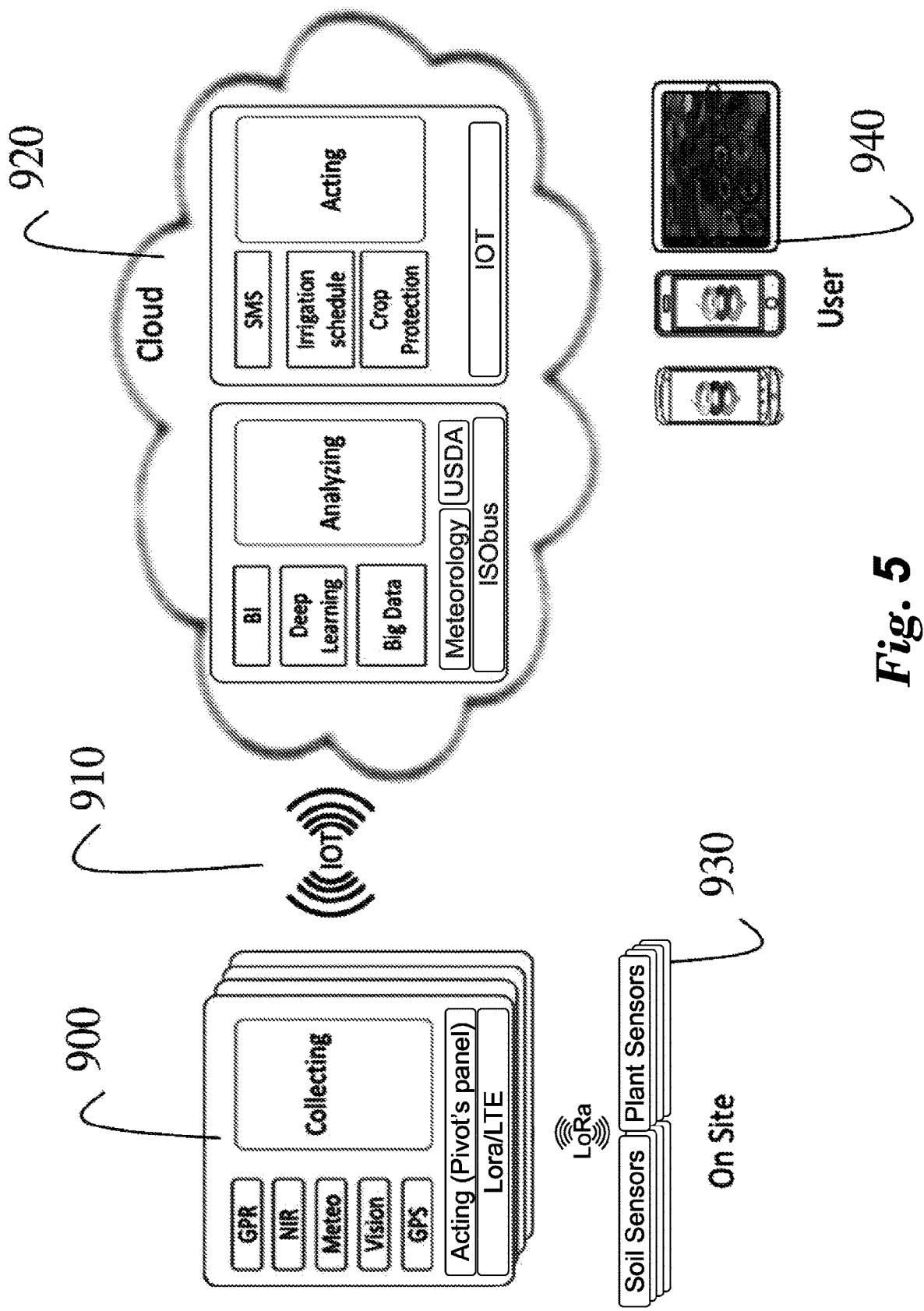
FIG. 5 is a schematic diagram of a system for automatically managing a plurality of center pivot irrigation machines.

Reference is now made to FIG. 5, showing a schematic diagram of a system for automatically managing a plurality of center pivot irrigation machines. The system includes four parts which are the following: (1) a cloud-based server; (2) a plurality of end devices configured for controlling center pivot irrigation machines; (3) a plurality of external soil and plant sensors disposed on croplands; and (4) a user's device enabling the user to communicate to the server and end devices.

The cloud-based server includes an analytical unit and a control unit. The analytical unit is configured for analyzing data on the basis of big data and deep learning technology. Real time meteorological data and forecasts are taken into account in the analysis. The analysis is carried out on the basis of regulations of the US agriculture department. In exemplary manner, the analytical unit is configured for recognizing image patterns indicating specific plant diseases.

The control unit is configured for establishing an irrigation schedule and crop protection program on the basis of obtained analysis. The control unit transmitted commands to the end devices. The commands are directed to control the end devices actuating fertigation valves of the center pivot irrigation machines.

A plurality of end devices is attached to the center pivot irrigation machines. Each end device further comprises: a ground penetration radar, an image sensor, a weather sensor, a GPS sensor, a collecting unit, a transponder and an actuator.

The ground penetration radar obtains volumetric water content data pertaining to croplands treated by said plurality of center pivot irrigation machines. The image sensor captures images of the croplands under the center pivot irrigation machines. The weather sensor measures real-time parameters of surrounding weather such that temperature, relative humidity and wind speed. The collecting unit interrogates data from said ground penetration radar, image sensor, weather sensor and GPS sensor. The transponder transmits collected data to the cloud-based server and receives control commands from it. The actuator controls said center pivot irrigation machine on the basis of said control commands.

External sensors are disposed on the ground cultivated plants and provide data to the cloud-based server.

The user devices display crop conditions in graphic and digital forms and transmit user commands to said cloud-based server.

Figure 6:
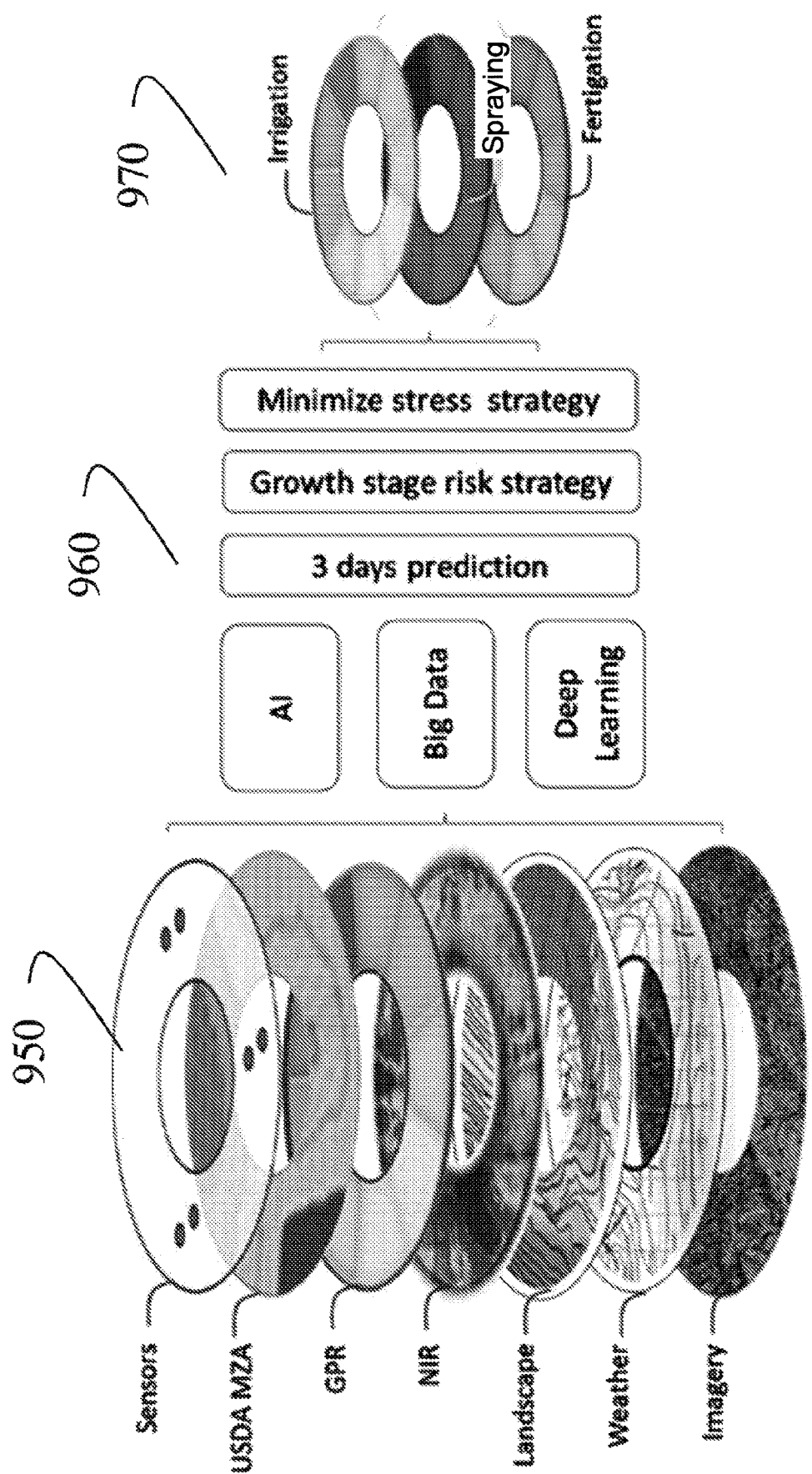
FIG. 6 is a workflow diagram for turning data into autonomous Irrigation, Fertigation, and Crop protection plans.

Reference is now made to FIG. 6 is a workflow diagram for turning data into autonomous Irrigation, Fertigation, and Crop protection plans.

Figure 7:
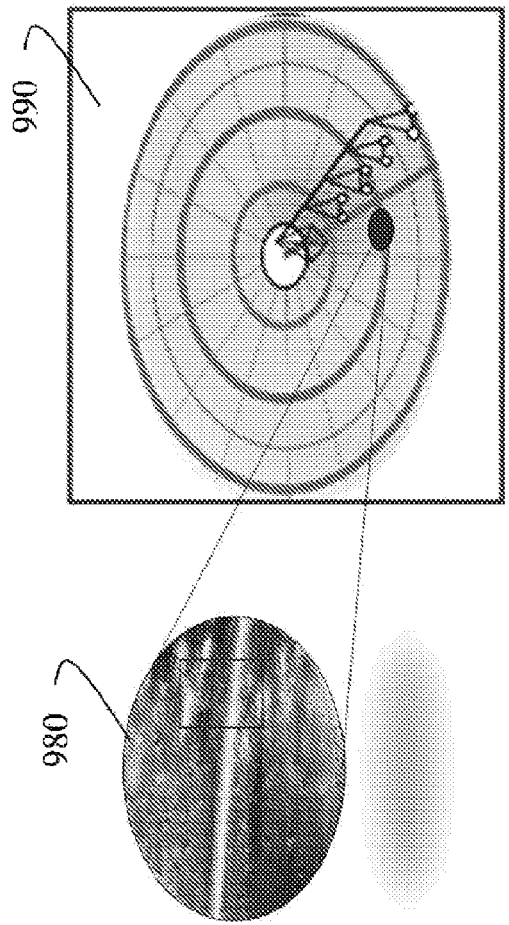
FIG. 7 is a schematic illustration of autonomous symptoms dictation to autonomous spraying.

Reference is now made to FIG. 7 is a schematically illustration of autonomous symptoms dictation to autonomous spraying.

Figure 8B:
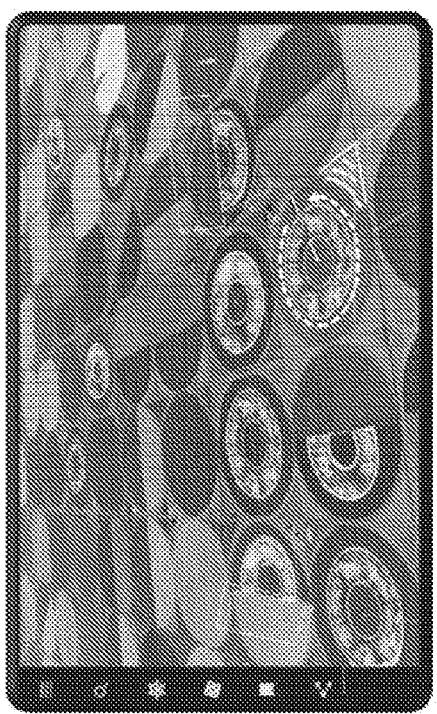
FIG. 8b is a UI illustration of displaying nitrogen stress condition.
Figure 8A:
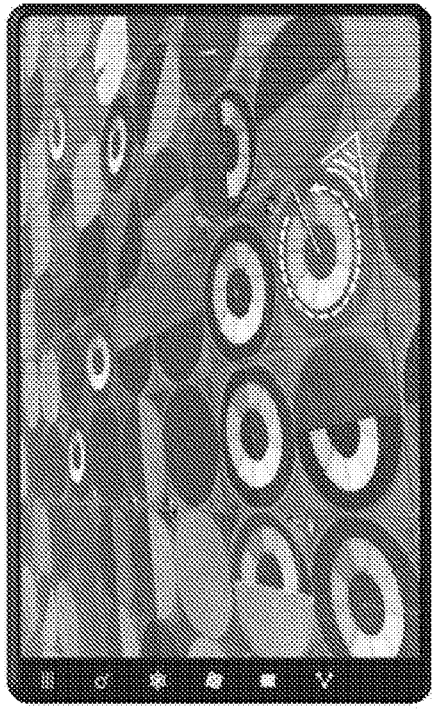
FIG. 8a is a UI illustration of displaying water stress condition per slice.

Reference is now made to FIG. 8a is a UI illustration for displaying water stress condition per slice.

Reference is now made to FIG. 8b is a UI illustration for displaying nitrogen stress condition.

Figure 9:
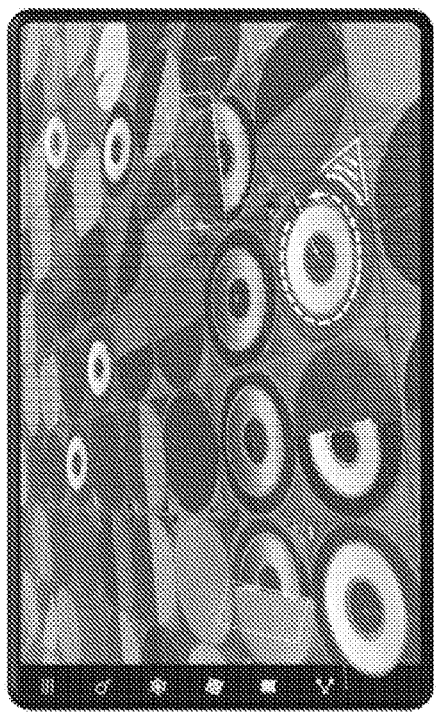
FIG. 9 is a schematic illustration of autonomous Social Crop protection by recognizing disease condition and alerting its neighbors.

Reference is now made to FIG. 9 is a schematically illustration of autonomous Social Crop protection. The pivot discovers disease condition and alerts its neighbors.

Figure 10:
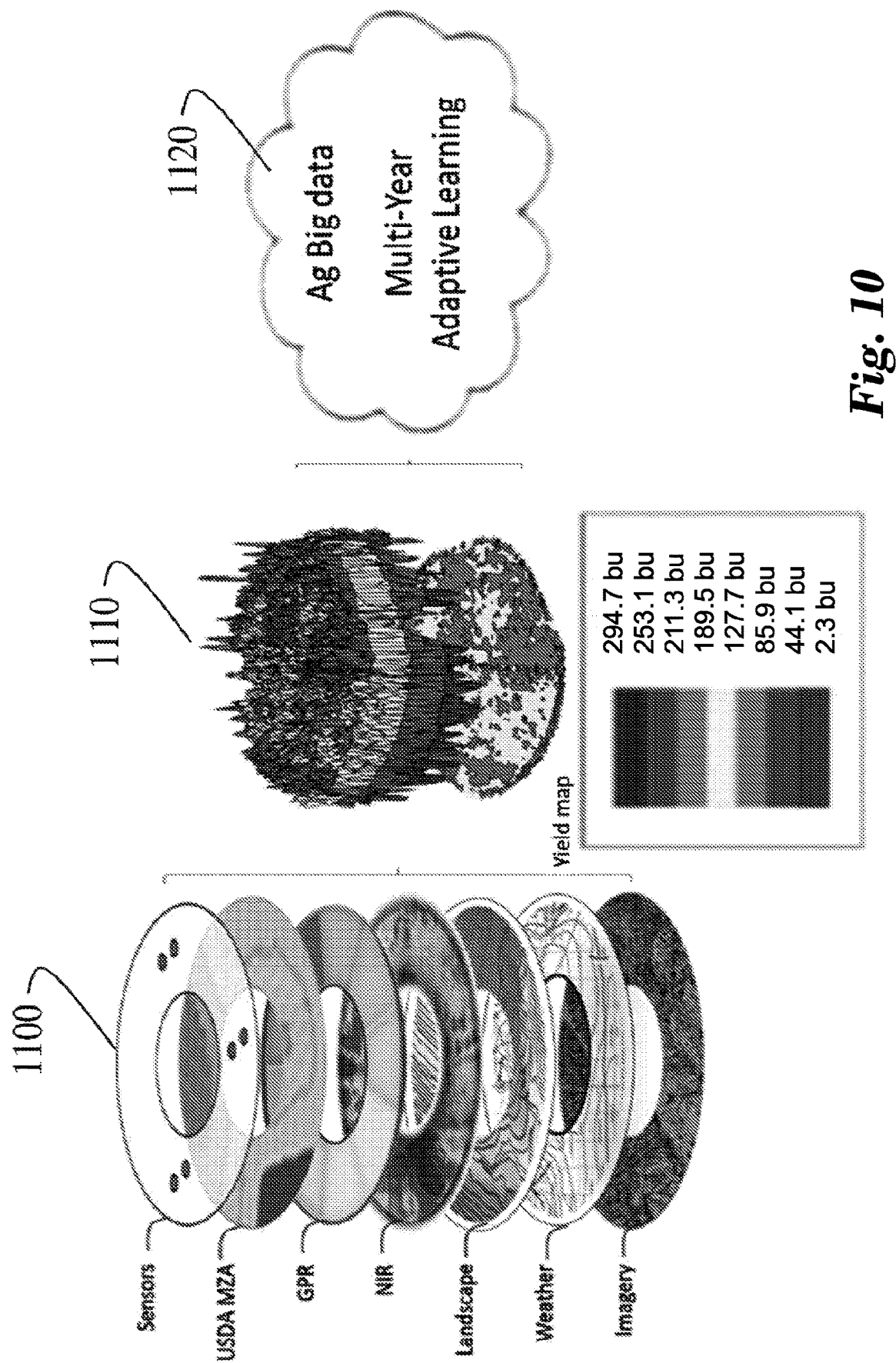
FIG. 10 is a workflow diagram of collecting annual data and applying adaptive learning based on correlation between yield maps and stress maps.

Reference is now made to FIG. 10 is a workflow diagram for turning data into year to year Adaptive learning based on correlation of one-year yield maps 1200 to one-year history multilayer stress map 1100 providing multi-year data of adaptive learning conclusions 1120.

Figure 11A:
FIG. 11a is a photograph of a field with fully grown corn plants, demonstrating drawbacks and disadvantages of the prior art.

Reference is now made to FIG. 11a, showing a photograph of a field with fully grown corn plants, the corn being about 2.5 meters high. FIG. 11a demonstrates disadvantages and drawbacks of the existing approach to measuring soil content data using a Ground-Penetrating Radar (GPR), such as disclosed by Tan et al., wherein a GPR antenna is mounted on a pivot arm of a center pivot irrigation machine, at a position corresponding to a location of a camera as used for capturing the photograph shown in FIG. 11a. The antenna is aimed at the ground at a wide angle, e.g. at about 60 degrees or the like.

As exemplified in FIG. 11a, a first apparent drawback of the prior art approach is that there is no direct, clear Line-of-Sight (LOS) to the ground. Rather, a pulse wave transmitted by an antenna mounted on the pivot arm may hit a varying number of corn plants on its way to the ground level surface, thus giving rise to measurement inconsistencies that are unrelated to the soil content. A second apparent drawback is that in case a traditional planting pattern consisting of straight lines plant rows is used, the pivot arm may cross those lines while traveling. This may similarly result in measurement variation that is unrelated to the soil content, as locations of crop rows in the antenna footprint are constantly changing.

One technical problem dealt with by the disclosed subject matter is to perform near surface, remote measuring of soil content in a field environment under general conditions, including but not limited to scenarios wherein the crops are masking the soil, being tall and dense, thereby rendering conventional approaches and pre-existing methods ineffective for said purpose.

Another technical problem dealt with by the disclosed subject matter is to avoid or mitigate measurement variation unrelated to soil content, as may be suffered when performing measurements using data sensing devices located above plant canopy, and/or due to perpetual changes in locations of crop rows in a footprint of such sensor as it travels along and across a field environment, particularly wherein a traditional planting pattern in straight lines being employed. On the other hand, in case additional installations are employed, such as a boom arm accommodating an antenna at a height below plant canopy, the boom may constantly cross crop rows and both the antenna and the crop may be damaged by result.

Yet another technical problem dealt with by the disclosed subject matter is to measure content data of planted crops in a field environment, such as, for example, water content or the like. Determining content of key components of plants, and water content in particular, up to a resolution of even a singular plant, may be instrumental in various applications, ranging from treatment plan establishment through anomaly detection (useful for example to early discovery of plant diseases before overall spread thereof to entire plots) to further, more elaborate patterns recognition and predictions provision accordingly based on historical and current information analysis, using techniques such as data mining, machine learning, artificial intelligence, big data manipulation, and the like.

One technical solution is to provide at least two data sensing devices, such as radar antennas or the like, deployed in an array arrangement and configured each for implementing a different functionality. A first data sensing device in the array arrangement may be configured for measuring data based on which a location of at least a pair of neighboring plant rows may be detected. A second data sensing device in the array arrangement may be configured for measuring soil content data, such as soil water content or the like. Spatial positioning and translation of the second data sensing device within the field environment, and relative to one or more locations of plant rows, such that measurements obtained by the second data sensing device may not suffer interference from plants or plant portions, may be guided by locations of neighboring plant row pairs, as determined based on the data measured by the first data sensing device. Put differently, the first data sensing device provides a functionality of detecting an unplanted space adjacent to a given row of plants, and the second data sensing device provides a functionality of measuring soil content data in an effective manner, being achieved, inter alia, by means of positioning the second data sensing device in said unplanted space, such that a direct Line-of-Sight (LOS) to the ground is thereby provided.

In some exemplary embodiments, the first data sensing device may be positioned relative to crop rows so as to acquire data at a wide Field-of-View (FOV). For the sake of clarity, and without loss of generality, in the context of the present disclosure, the terms "Field-of-View (FOV)", "angle of view", or simply "angle", may be used interchangeably and refer to an angle between a perpendicular from a position of a data sensing device to the ground, on one hand, and a direction at which a focal center of said data sensing device is aimed at towards the ground, on the other hand. Accordingly, a wide FOV may refer to an angle in a range of about 45 degrees to about 75 degrees, or the like, whereas a narrow FOV may refer to an angle in a range of about 0 degrees to about 20 degrees, or the like.

In some exemplary embodiments, the second data sensing device may be positioned relative to crop rows so as to acquire data in a narrow FOV. Additionally or alternatively, the second data sensing device may be positioned relative to crop rows so as that a locus of measurements performed thereby is comprised in an unplanted space between a pair of neighboring rows. Additionally or alternatively, the second data sensing device may be positioned relative to crop rows such that a direct Line-of-Sight (LOS) to the ground is provided, e.g., the second data sensing device may be located below a canopy layer of the crop rows. As an illustrative example, in case of soy or corn plants, which, when fully grown, may rise up to a height above the ground of about 2.5 meters or the like, such as those crops portrayed in FIG. 11a, the second data sensing device may be positioned at a height above the ground of about 1 meter or the like.

In some exemplary embodiments, the first, second, or both data sensing devices may be devices emitting electromagnetic radiation, such as radar antennas, Light Direction-and-Ranging (Lidar) sensors, or the like. In the context of the present disclosure, the term "beam" may be used in a similar sense as the terms FOV, angle and the like, and refer to an extent of a target area being exposed to transmitted signals of said data sensing devices. For example, a wide beam may be considered synonymous with a wide FOV, a narrow beam may be considered synonymous with a narrow FOV or narrow angle, and so forth.

In some exemplary embodiments, the first data sensing device may be accommodated by a first support member, so as to maintain the first data sensing device at a desired position and/or orientation, thereby obtaining a desired predetermined FOV. Similarly, the second data sensing device may be accommodated by a second support member, so as to maintain the second data sensing device at a position and/or orientation for obtaining a desired predetermined FOV, optionally different than the FOV associated with the first data sensing device. In some exemplary embodiments, the first and second support members may be integrated together in a single physical structure. Alternatively, the first and second support members may be two separate, independent units.

In some exemplary embodiments, the second support member accommodating the second data sensing device may be coupled to a spatial translation mechanism, configured for mobilizing the second support member within the field environment. In some further exemplary embodiments, the spatial translation mechanism may be configured to translate the second data sensing device such that measurements obtained thereby trace a trajectory along and within an unplanted space adjacent to a given row of plants, which a location thereof being determined based on data measured by said first data sensing device, as disclosed herein.

In some exemplary embodiments, a center pivot irrigation system may be deployed in a field environment, such as the field environment captured in FIG. 11a. A pivot arm of the center pivot irrigator may be utilized in role of said first support member. An additional arm, also referred to as "boom", may be coupled to the pivot arm and utilized in role said second support member. The additional arm may optionally be an articulated arm comprising at least two segments, a first of which being located proximally to the pivot arm and extending horizontally in an orientation substantially parallel to the ground, and second of which being located distally to the pivot arm and in a vertical direction towards the ground and substantially orthogonal thereto.

In some exemplary embodiment, an additional, third data sensing device for imaging or location data gathering may be provided so as to allow pinpointing of a location in the field environment wherein a data measurement or sample originated from. An imaging sensor for use in role of said third data sensing device may be, for example, a digital camera such as a Charge Coupled Device (CCD), Complementary Metal Oxide Semiconductor (CMOS) or likewise sensor camera, a Time-of-Flight (ToF) camera, an acoustic imaging sensor, such as ultrasonic device, or the like. A location sensor for use in role of said third data sensing device may be, for example, a Global Positioning System (GPS) sensor, a Near-field Communication (NFC) sensor, a Radio-frequency identification (RFID) sensor, or the like.

Another technical solution is to employ a circular planting pattern, wherein plants are being planted in rows formed in a circle shape. The plurality of circles of plant rows thus formed may be concentric and with successively increasing radii. The circles may be spaced apart from one another by a constant distance, similarly to the spacing between crop rows in traditional linear planting pattern. In some exemplary embodiments, a center pivot irrigation system may be employed, wherein the pivot span may be utilized to define the radius of the outermost circle of the plurality of plant row circles, or an upper bound thereon.

Yet another technical solution is to perform a synthesis of content data measured by two or more sensing devices differing from one another in functionality, wherein a footprint of a first sensing device of the two or more sensing devices comprises a portion of a crop row and an adjacent portion of an unplanted soil region, wherein a footprint of a second sensing device of the two or more sensing devices comprises said adjacent portion of an unplanted soil region, such that by means of correlation and subtraction of substantially collocated, overlapping and optionally simultaneously obtained content data measurements, respective content data of said crop row portion may be determined.

In some exemplary embodiments, the first data sensing device may be a wide FOV sensor and the second data sensing device may be a narrow FOV sensor, wherein the first and second sensing devices being positioned in an array arrangement and directed towards the ground each in respective orientations such that each field region portion captured by the first data sensing device per sample encompasses a field region portion captured by the data second data sensing device per sample, for each pair of instantaneous samples obtained thereby.

In some exemplary embodiments, the first and second data sensing devices may be mounted on a center pivot irrigation system, as disclosed herein. In some further exemplary embodiments, the center pivot irrigation system may be deployed in a field environment having a linear-like planting pattern of crop rows. The center pivot irrigation system may be driven in a rotary motion around a center axis thereof, whereby a pivot arm sweeps a disk-like area of the field environment in each completed circulation about the center point. Data measurements or samples obtained by the first and second data sensing devices may comprise data acquired within sectors or arc-like regions of the field environment, wherein respective trajectories traversed by the first and second data sensing devices alternately cross planted crop rows and unplanted ground areas there-between or there aside at varying angles relative to a line direction parallel or tangential to said rows. As result, a speed rate or frequency of alternation between successive groups of measurements or samples which correspond to neighboring plant rows and one or more regions of bear soil adjacent thereto or in between thereof, respectively, may vary as a function of a relative orientation or angle between the straight lines by which the plurality of planted crops are formed and the pivot arm's pose in its temporary or general whereabouts during a time in which said samples being acquired.

In some exemplary embodiments, a first dataset comprised of samples obtained by the first sensing device having a wide FOV may be analyzed to determine a momentary frequency of alternation between crop/soil-originated samples within the first dataset. The momentary frequency thus determined may then be used to identify or differentiate between crop/soil-originated samples in a second dataset obtained by the second sensing device having a narrow FOV, wherein the first and second dataset being obtained substantially at a same time and place, i.e. same sector or arc region in the field environment. Once the samples in the second dataset are sorted to crop- or soil-originated measurements, a content value of a crop portion, or even a particular plant or group of plants, may be determined by means of subtracting a measured content value of a soil portion from a measured content value of said crop portion or plant, as recorded in the second dataset.

One technical effect of utilizing the disclosed subject matter is to provide a solution for measuring soil content with a GPR device in a tall and dense crop field, which previously has not been successfully accomplished.

Another technical effect of utilizing the disclosed subject matter is to overcome rough soil surface inaccuracies that a GPR device may encounter when located above plant canopy, e.g. when mounted on a pivot arm in a center pivot irrigation system, as proposed by previous approaches.

Yet another technical effect of utilizing the disclosed subject matter is to provide an improved controlled sensing environment, by means of an installation that is relatively close to the ground and using a narrow beam, thereby enabling isolation of readings that may be affected by crop, and allowing obtaining of substantially noise-free ground readings.

Yet another technical effect of utilizing the disclosed subject matter is to obtain a region or sector (e.g., a ring or the like, such as when used in a field under an irrigation pivot) of dense, volumetric soil content measurements, such as, for example, Volumetric Water Content (VWC) or any likewise physical quantity, as opposed to few specific measurements, such as the ones that may be obtained when using an in-ground soil sensor.

The disclosed subject matter may provide for one or more technical improvements over any pre-existing technique and any technique that has previously become routine or conventional in the art. Additional technical problems, solutions and effects may be apparent to a person of ordinary skill in the art in view of the present disclosure.

Figure 11B:
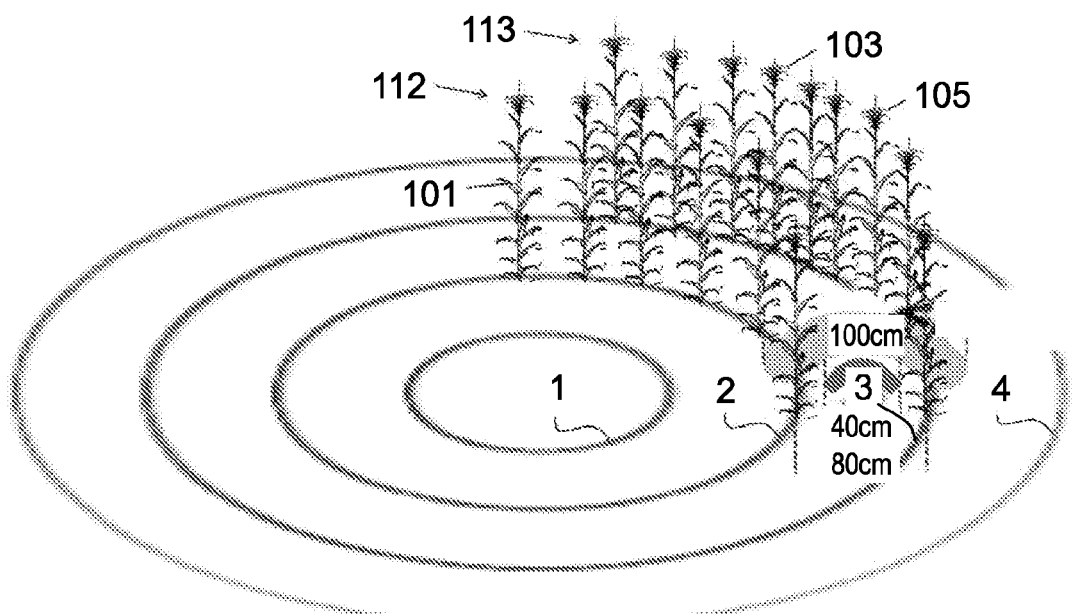
FIG. 11b is a schematic illustration of a field environment in which the disclosed subject matter may be utilized, in accordance with some exemplary embodiments of the disclosed subject matter.

Reference is now made to FIG. 11b, showing a schematic illustration of a field environment in which the disclosed subject matter may be utilized, in accordance with some exemplary embodiments of the disclosed subject matter.

FIG. 11b schematically illustrates a field environment comprising a plurality of plants, such as Plant 101, Plant 103, and Plant 105, the plurality of plants being planted in a circular-like plantation pattern. The circular-like plantation pattern comprises a plurality of row-like elements, such as Row 112 and Row 113. Each row-like element comprises a plurality of plants, being planted side by side at substantially equidistant spaces between one another. Each row-like element is formed at a circle-like geometric shape, which circle-like shapes corresponding to the plurality of row-like elements are substantially concentric, with successively increasing radii, such as Circle 1, Circle 2 corresponding to Row 112, Circle 3 corresponding to Row 113, and Circle 4. The plurality of plants in each row-like element may be planted such that each plant's center, i.e. a projection of its central axis on the ground level, is located substantially on the corresponding circle-like shape, as exemplified in FIG. 11*b*. The plurality of row-like elements may be spaced apart from one another by a predetermined distance, e.g. of about 80 centimeters, as illustrated in FIG. 11*b*.

In some exemplary embodiments, and as illustrated in FIG. 11*b*, the plurality of plants may have substantially uniform dimensions, e.g. a total width or horizontal diameter of about 40 centimeters, comprised of plant leaves or likewise canopy parts extending from a stem or central core, at a length of about up to 20 centimeters in each direction, such that a portion of the soil between two neighboring plant rows that is exposed of any crops or crop parts, has a predetermined width, e.g. of about 40 centimeters, and a total diameter of a pair of neighboring plant rows has a predetermined length, e.g. of about 100 centimeters.

Figure 12A:
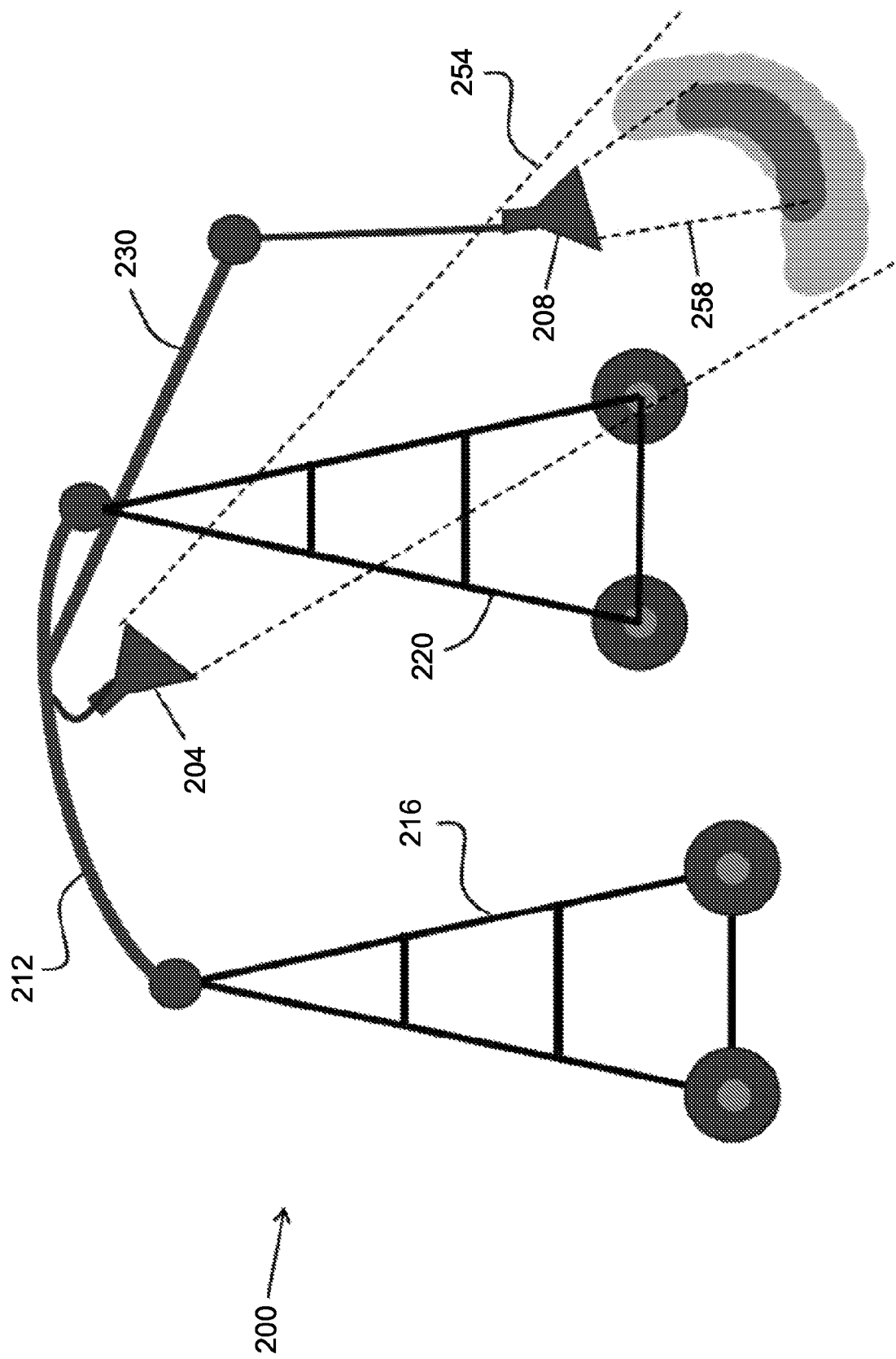
FIGS. 12a-12e are schematic illustrations of a perspective, top and side view, respectively, of a device for measuring field content data, and of said device in operation relative to a field environment comprising crops in row-like plantation pattern, from top and perspective views, respectively, in accordance with some exemplary embodiments of the disclosed subject matter.
Figure 12B:
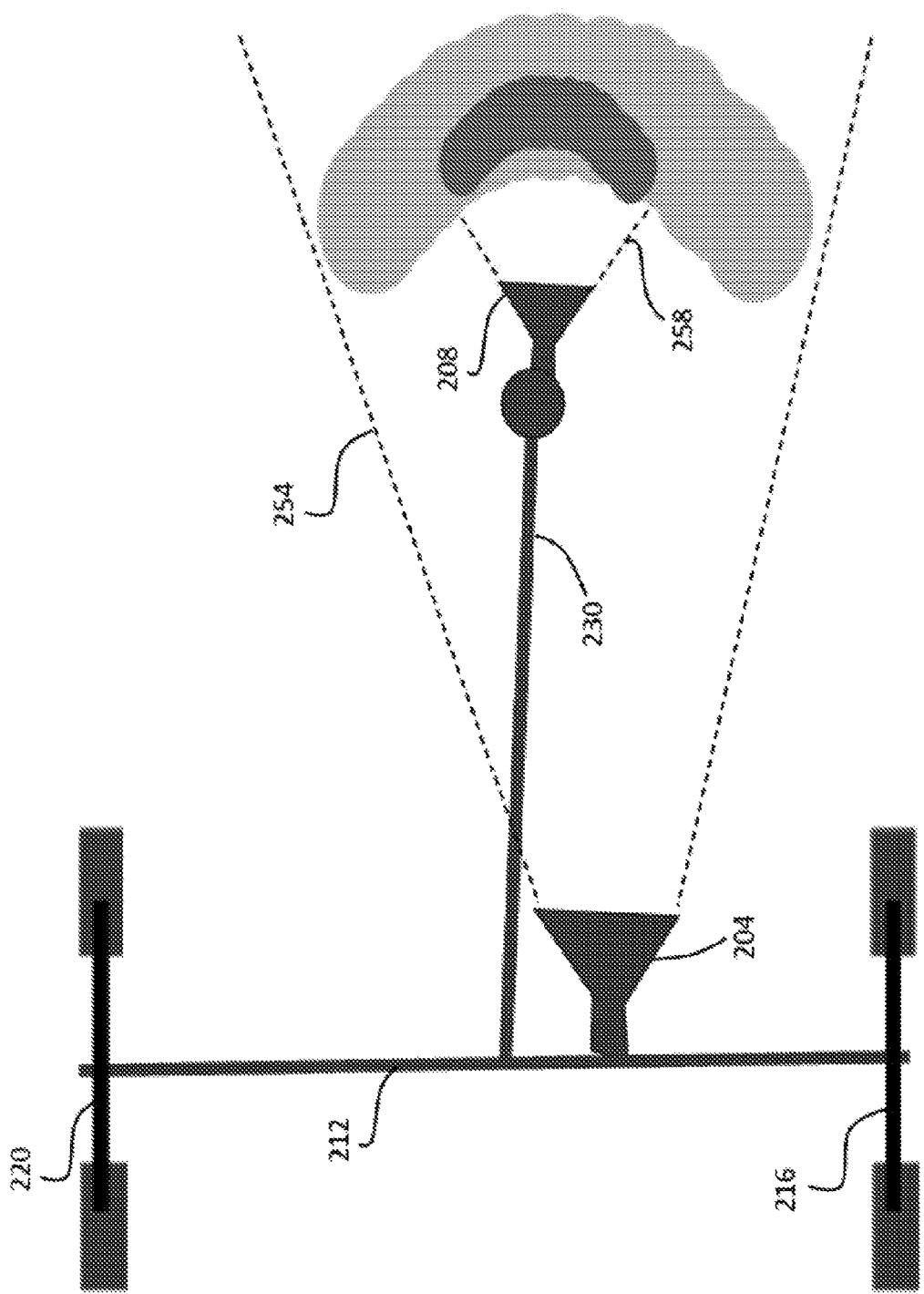
Figure 12C:
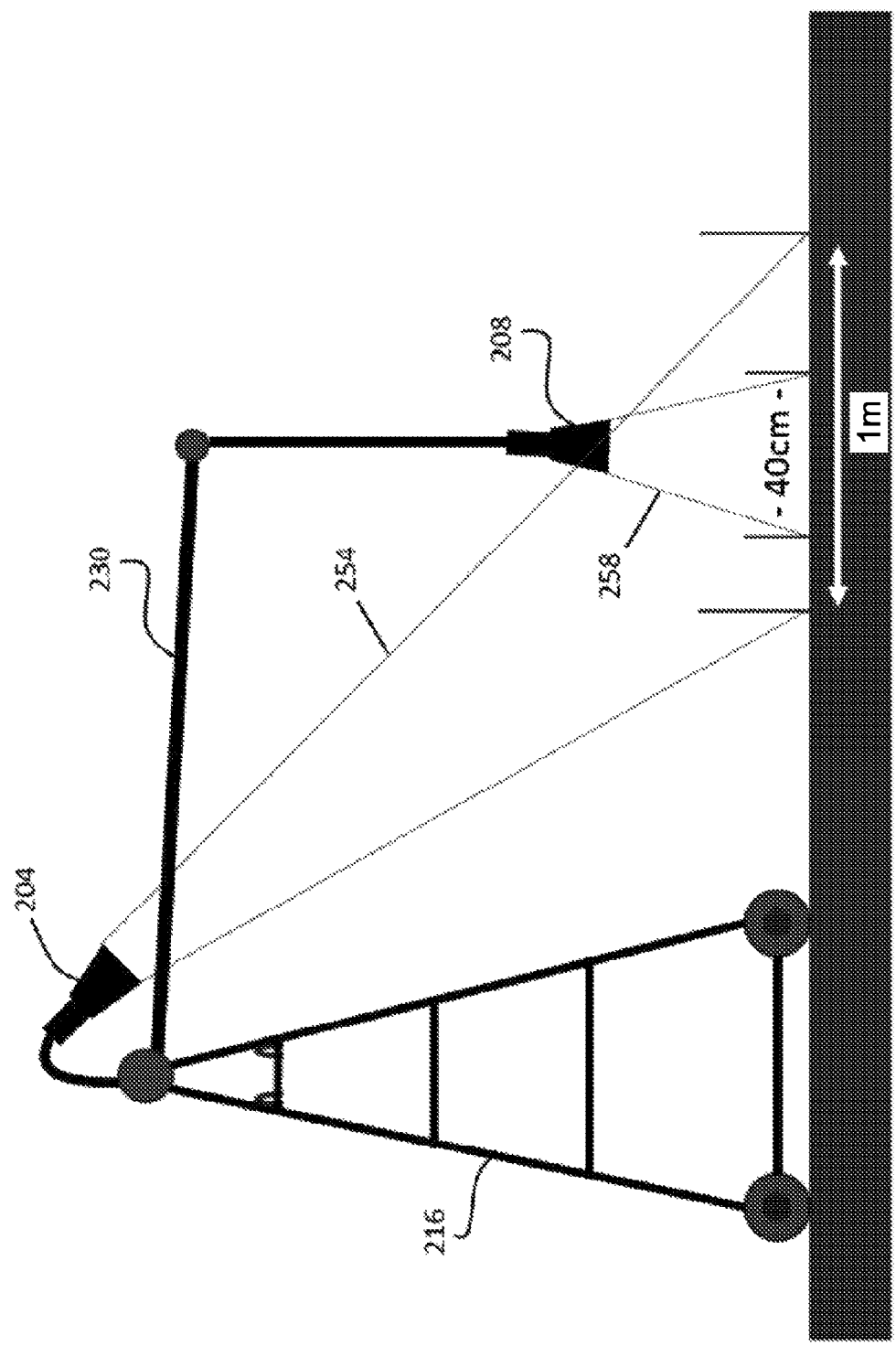
Figure 12D:
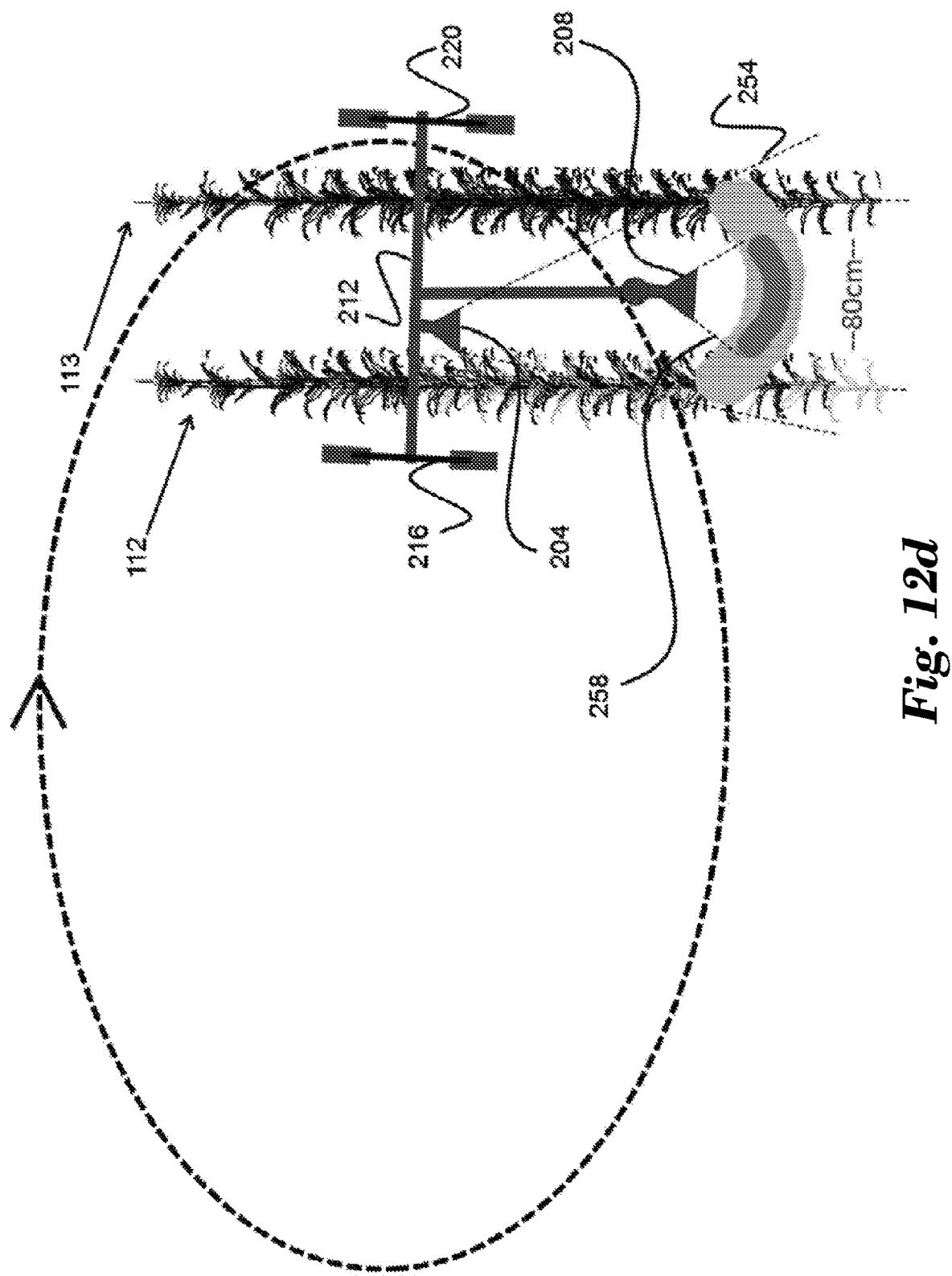
Figure 12E:
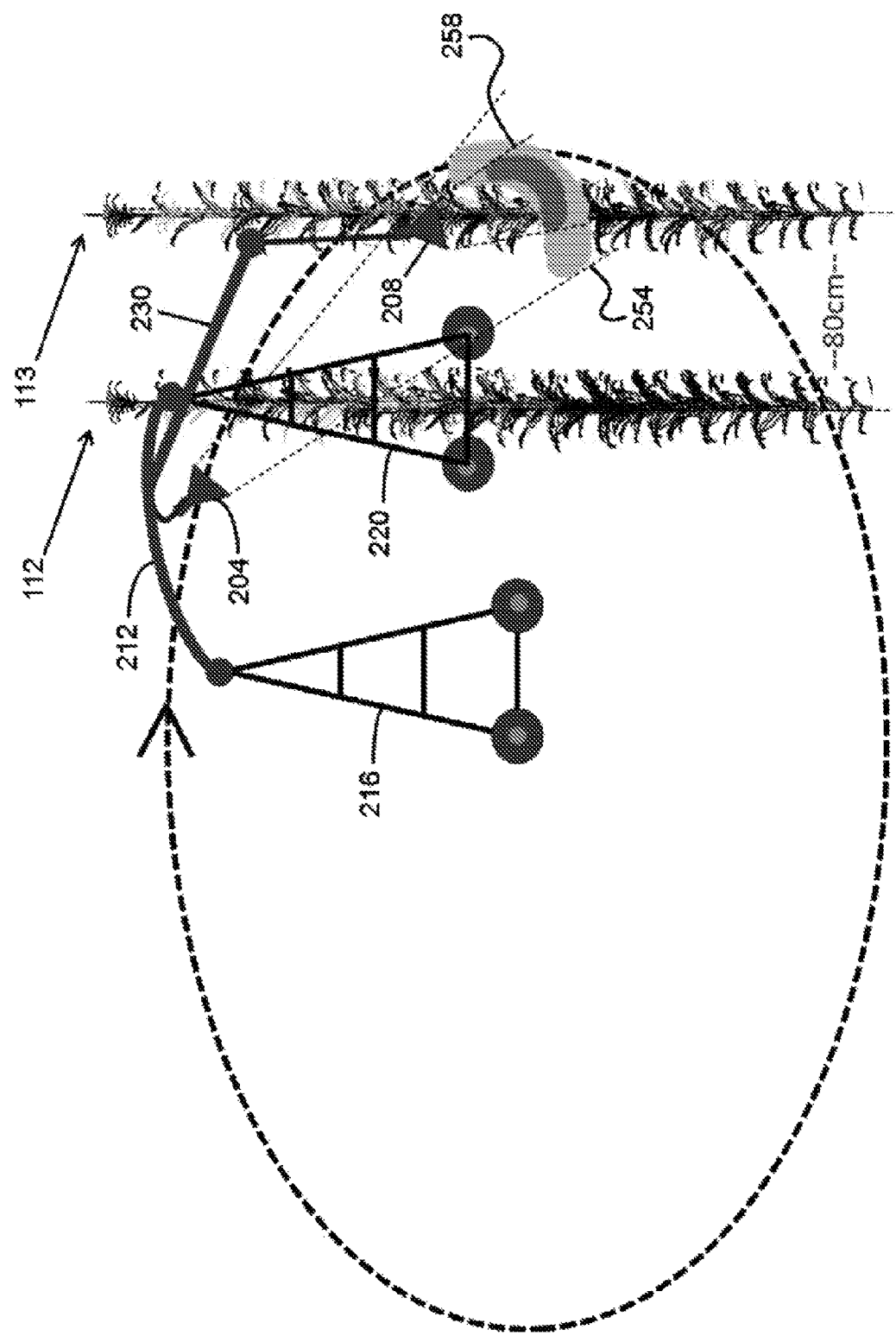

Reference is now made to FIGS. 12*a*-12*e*, showing each a schematic illustration of a device for measuring field content data, in accordance with some exemplary embodiments of the disclosed subject matter. For the sake of facilitating understanding of the disclosed subject matter, the schematic illustration of the device for measuring field content data is shown in FIG. 12*a* at a perspective view, in FIG. 12*b* at a top view, and in FIG. 12*c* at a side view. Similarly, the schematic illustration of the device when being deployed in operation relative to a field environment comprising crop rows planted in a circular plantation pattern, in accordance with some exemplary embodiments of the disclosed subject matter, is shown in FIG. 12*d* at a top view, and in FIG. 12*e* at a perspective view.

As demonstrated in FIGS. 12*a*-12*e*, a Device 200 may comprise at least two sensing devices, such as Antenna 204 and Antenna 208, disposed in an array arrangement relative to one another. Device 200 may comprise a first support member, such as Pivot Arm 212, configured for accommodating Antenna 204 at a first desired position relative to a field environment, and a second support member, such as Boom 230, configured for accommodating Antenna 208 at a second desired position relative to the field environment. In some exemplary embodiments, Pivot Arm 212 may be mounted on a base frame comprising one or more wheeled towers, such as Tower 216 and Tower 220. Boom 230 may be connected to Pivot Arm 212, either by a detachable attaching means, non-detachable attaching means, or integrally formed therewith as a single monolithic unit. Boom 230 may be an articulated arm, such as illustrated in FIGS. 12*a*-12*e*.

As further demonstrated in FIGS. 12*a*-12*e*, Antenna 204 may be configured to provide a wide field of view (FOV) 254, such that FOV 254 embraces at least two rows of crop plants as planted in the field environment, similarly as shown in FIG. 11*b*, wherein a maximal distance between extremal edges of crop plants at two neighboring rows may be of a first predetermined length, e.g. of about 100 cm. In contrast, Antenna 208 may be configured to provide a narrow field of view (FOV) 258, such that FOV 258 encompasses an unplanted space between two neighboring rows of crop plants, such as shown in FIG. 1*b*, wherein a minimal distance between extremal edges of crop plants at two neighboring rows may be of a second predetermined length, being encompassed by the first predetermined length, e.g. of about 40 cm.

Figure 13A:
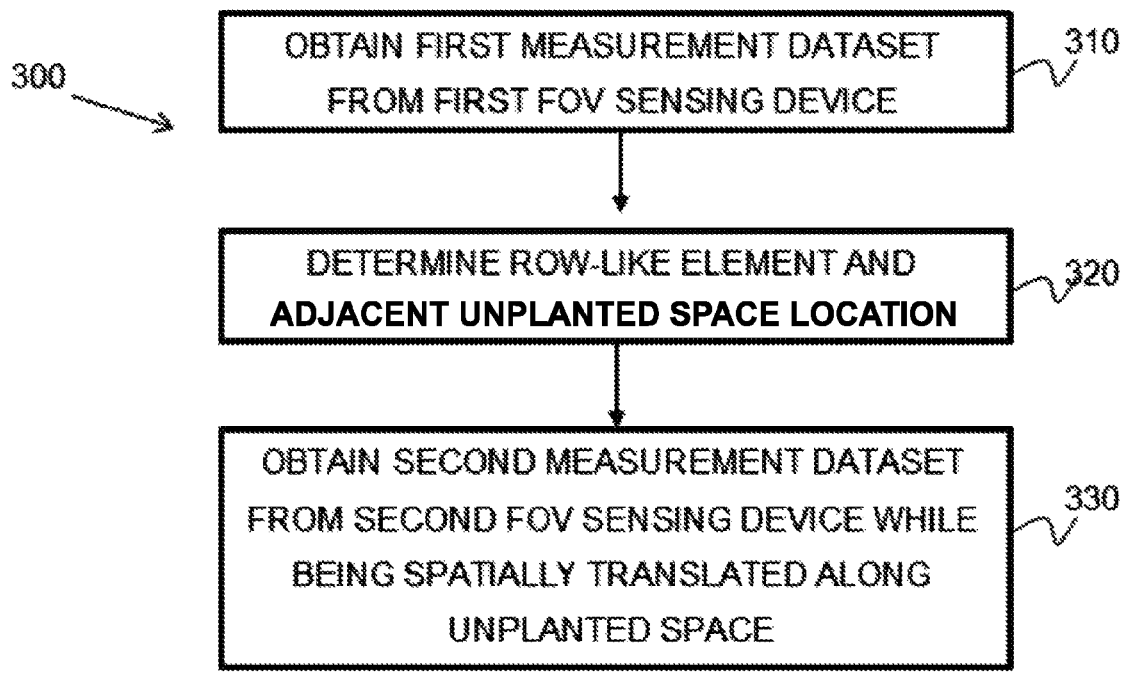
FIGS. 13a-13b are flowchart diagrams of methods of measuring field content data, in accordance with some exemplary embodiments of the disclosed subject matter.

Reference is now made to FIG. 13*a* showing a flowchart of a method for measuring field content data, in accordance with some exemplary embodiments of the disclosed subject matter. The Method 300 shown in FIG. 13*a* may be implemented in a field environment comprising a plurality of plants arranged in a plantation pattern comprising a plurality of row-like elements, spaced apart from one another by at least a predetermined distance, such that for each row-like element, at least one adjacent unplanted space may be formed there-along.

On Step 310, a first measurement dataset may be obtained. The first measurement dataset may be obtained using a first data sensing device, such as Antenna 204 of FIGS. 12*a*-12*c*, configured for obtaining a first type of measurement dataset comprised in a first field-of-view (FOV), such as FOV 254 FIGS. 12*a*-12*c*. The first data sensing device may be accommodated by a first support member in a position at a first height relative to a ground level of the field environment which Method 300 being carried out therein. The first height may be determined based on a first threshold, which may be, for example, a function of a maximal height of crop plants planted in the field environment or the like.

On Step 320, a location of at least a first row-like element of the plurality of row-like elements, and a location of a first adjacent unplanted space corresponding to the first row-like element, may be determined. The locations of the first row-like element and the first adjacent unplanted space corresponding thereto may be determined based on data analysis of the first measurement dataset.

On Step 330, a second measurement dataset may be obtained. The second measurement dataset may be obtained using a second data sensing device, such as Antenna 208 of FIGS. 12*a*-12*c*, configured for obtaining a second type of measurement dataset comprised in a second field-of-view (FOV), such as FOV 258 FIGS. 12*a*-12*c*. The second data sensing device may be accommodated by a second support member in a position at a second height relative to the ground level, said second height being determined based on a second threshold, which may be, for example, a function of a minimal height of crop plants' canopy, a range of water sprinklers deployed in the field environment, a combination of both the former and the latter, or the like.

In some exemplary embodiments, the second measurement dataset may be obtained while spatially translating the second data sensing device along a trajectory longitudinally traversing the first adjacent unplanted space. The spatial translation may be effected responsive to a control command, which may be outputted based on the location of the first adjacent unplanted space determined.

Figure 13B:
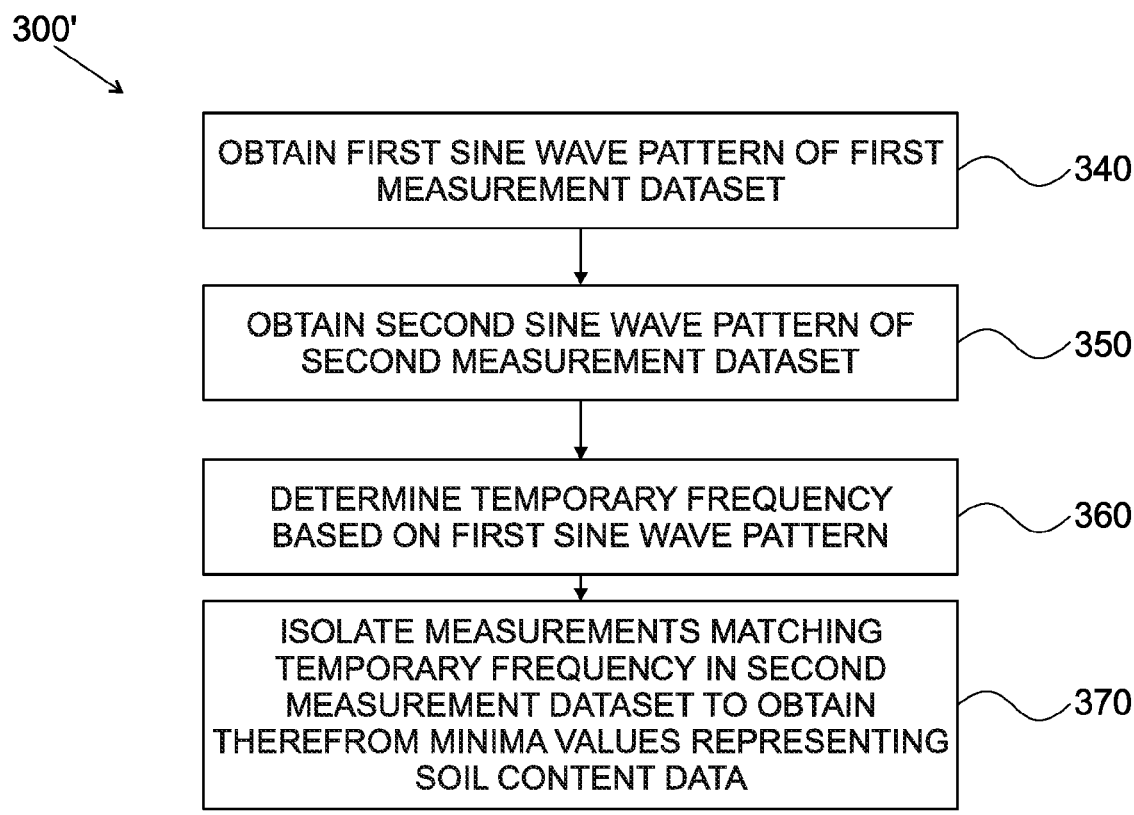

Reference is now made to FIG. 13*b* showing a flowchart of a method for measuring soil content data, in accordance with some exemplary embodiments of the disclosed subject matter. The Method 300' shown in FIG. 13*b* may be employed in a scenario wherein a pattern plantation of crop plants in the field environment is linear rather than circular-like, namely, the plurality of row-like elements are in a form of straight lines. A center pivot irrigation may be deployed in the field environment and utilized as a base frame accommodating an array of sensing devices at different functional configuration, e.g. wide versus narrow footprint, in accordance with the disclosed subject matter On Step 340, a first sine wave pattern associated with a first measurement dataset, such as the first measurement dataset obtained on Step 310 of FIG. 13a, may be obtained.

On Step 350, a second sine wave pattern associated with a second measurement dataset, such as the second measurement dataset obtained on Step 320 of FIG. 13a, may be obtained.

On Step 360, a temporary frequency may be determined based on the first sine wave pattern. The temporary frequency may be considered as corresponding to a temporary angle between a pivot arm of the pivot irrigation system and at least one crop row being crossed thereby while the pivot arm circularly travels in the field environment, such that the array of sensing devices mounted thereon may capture measurements of crop rows and/or unplanted space between crop rows at a varying different rate, as a function of the changing temporary angle.

It will be appreciated by a person skilled in the art that the first sensing device having a wide FOV may obtain measurements averaging one or two crop rows and the bare ground between or beside them, and therefore results in a relatively shallow sine wave pattern, with a slowly changing frequency. In contrast, the second sensing device having a having a narrow FOV may obtain measurements averaging zero or one crop row with the adjacent or surrounding unplanted space, at a same frequency. Such measurements may be noisy as properties of crops (i.e. structure, water content, and the like) and soil (e.g., surface, texture, composition, and the like) may be diverse. Thus, finding the momentary frequency of the measurement may be of significant importance to overcome this diversity. The narrow FOV measurements may be expected to be much noisier, but to provide singular accurate readings of soil only areas as well as of areas consisting mostly of a crop row. In contrast, the wide FOV measurements may be expected to be less noisy and provide a better reading for frequency extraction.

On Step 370, based on the temporary frequency determined on Step 360 and the second sine wave pattern obtained on Step 350, measurements which exhibit a frequency matching to the temporary frequency may be isolated within the second measurement dataset. In some exemplary embodiments, frequency matching may be performed by correlating the first and second sine wave pattern in the frequency domain and applying an appropriate band pass filter. Those narrow FOV measurements that fit the temporary frequency may be expected to be accurate with a higher likelihood as compared with the remainder measurements, where minima values may be expected to be representative of purely soil content data, and maxima values as representing crop row measurements.

The invention claimed is:

1. A method of measuring soil content data, said method being adapted for implementation in a field environment comprising a plurality of plants arranged in a plantation pattern comprising a plurality of row-like elements, wherein said plurality of row-like elements being spaced apart from one another by at least a predetermined distance, whereby for each of which row-like elements at least one adjacent unplanted space is defined; said method comprising the steps of:
    obtaining a first measurement dataset using a first data sensing device configured for obtaining a first type of measurement dataset comprised in a first field-of-view (FOV), wherein said first data sensing device being accommodated by a first support member in a position at a first height relative to a ground level of said field environment, said first height being determined based on a first threshold;
    determining, based on data analysis of the first measurement, dataset:
        a location of at least a first row-like element of the plurality of row-like elements; and,
        a location of a first adjacent unplanted space corresponding to said first row-like element;
    and,
    obtaining a second measurement dataset using a second data sensing device configured for obtaining a second type of measurement dataset comprised in a second FOV, said second data sensing device being accommodated by a second support member in a position at a second height relative to the ground level, said second height being determined based on a second threshold;
    said obtaining the second measurement dataset is performed while said second data sensing device being spatially translated along a trajectory longitudinally traversing said first adjacent unplanted space, which spatial translation being effected responsive to a control command outputted based on the location of the first adjacent unplanted space determined;
wherein responsive to a determination that said plantation pattern is linear, performing the further steps of:
    obtaining a first sine wave pattern associated with the first measurement dataset;
    obtaining a second sine wave pattern associated with the second measurement dataset;
    determining, based on the first sine wave pattern, a temporary frequency corresponding to a temporary angle between one or more row-like elements of the plurality of row-like elements and said first support member accommodating said first, sensing device; and
    isolating within the second measurement dataset, based on the temporary frequency determined and the second sine wave pattern, one or more measurements exhibiting a frequency matching to the temporary frequency, to obtain therefrom minima values representative of measured soil content data.

2. Method according to claim 1, wherein at least one of the following is true:
    said plantation pattern is selected from the group consisting of: a linear pattern, wherein said plurality of row-like elements are shaped in a form of straight lines parallel to one another; and, a circular-like pattern, wherein said plurality of row-like elements are shaped in a form of concentric circles of successively increasing radii;
    said first and second data sensing devices are selected from the group consisting of: a Ground-Penetrating Radar (GPR) antenna; a Micropower Impulse Radar (MIR) antenna; a Light Direction And Ranging (LIDAR) sensor; and any combination thereof;
    said field environment further comprises a center pivot irrigation system deployed therein, wherein said first support member being comprised in a pivot arm of said center pivot irrigation system;
    said field environment further comprises a center pivot irrigation system deployed therein, wherein said second support member comprises an articulated arm extending from a pivot arm of said center pivot irrigation system;
    said first FOV being obtained by means of directing said first data sensing device at an angle towards a ground level of said field environment relative to a perpendicular from a position thereof to the ground level, which angle being selected from a range between about 45 degrees and about 75 degrees; and said second FOV being obtained by means of directing said second data sensing device at an angle towards a ground level of said field environment relative to a perpendicular from a position thereof to the ground level, which angle being selected from a range between about 0 degrees and about 20 degrees.

3. The method according to claim 1, wherein said first threshold is defined as a function of a maximal height of the plurality of plants, and wherein said second threshold is defined as a function of at least one of: a minimum height of a canopy of the plurality of plants; and, a range of one or more water sprinklers deployed in said field environment.

4. A system useful for measuring soil content data, said system being adapted for deployment in a field environment comprising a plurality of plants arranged in a plantation pattern comprising a plurality of row-like elements, wherein said plurality of row-like elements being spaced apart from one another by at least a predetermined distance, whereby for each of which row-like elements at least one adjacent unplanted space is defined; said system comprising:

a first data sensing device configured for obtaining a first ape of measurement dataset comprised in a first field-of-view (FOV);

a second data sensing device configured for obtain measurement dataset comprised in a second FOV;

a first support member configured for accommodating said first data sensing device in a position at a first height relative to a ground level of said field environment, said first height being determined based on a first threshold;

a second support member configured for accommodating said second data sensing device in a position at a second height relative to the ground level of said second height being determined based on a second threshold:

at least one spatial translation mechanism configured for spatially translating said first and second support members in response to control commands, thereby effecting spatial translation of said first and second data sensing devices;

an analyzing unit configured for determining, based on data analysis of a first measurement dataset obtained by said first data sensing device:

a location of at least a first row-like element of the like elements; and, a location of a first adjacent unplanted space corresponding to said first row-like element;

a control unit configured for outputting, based on the location of the first adjacent implanted space determined by said analyzing unit, a control command to said spatial translation mechanism in order to spatially translate said second data sensing device along a trajectory longitudinally traversing said first adjacent unplanted space; and, a data collection unit configured for collecting a second measurement dataset obtained by said second data sensing device while traversing said trajectory, wherein responsive to a determination that said plantation pattern is linear, the system is configured to:

obtain a first sine wave pattern associated with the first measurement data set;

obtain a second sine wave pattern associated with the second measurement dataset;

determine, based on the first sine wave pattern, a temporary frequency corresponding to a temporary angle between one or more row-like elements of the plurality of row-like elements and said first support member accommodating said first sensing device; and isolate within the second measurement dataset, based on the temporary frequency determined and the second sine wave pattern, one or more measurements exhibiting a frequency matching to the temporary frequency, to obtain therefrom minima values representative of measured soil content data.

* * * * *